United States Patent [19]

Gaillard-Kelly et al.

[11] Patent Number: 5,411,981
[45] Date of Patent: May 2, 1995

[54] PHENYLIMIDAZOLIDINES HAVING ANTIANDROGENIC ACTIVITY

[75] Inventors: Martine Gaillard-Kelly; Francois Goubet, both of Paris; Daniel Philibert, La Verenne Saint Hilaire; Jean-Georges Teutsch, Pantin, all of France

[73] Assignee: Roussel Uclaf, France

[21] Appl. No.: 64,257

[22] Filed: May 18, 1993

Related U.S. Application Data

[63] Continuation-in-part of Ser. No. 819,910, Jan. 9, 1992, abandoned.

[30] Foreign Application Priority Data

Jan. 9, 1991 [FR] France .................. 91 00185
Jul. 8, 1992 [FR] France .................. 92 08431

[51] Int. Cl.$^6$ .................. C07D 233/72; A61K 31/415
[52] U.S. Cl. .................. 514/386; 514/391; 514/342; 548/311.1; 548/317.1; 548/318.5; 548/320.1; 548/320.5
[58] Field of Search .................. 514/391, 386, 342; 548/317.1, 318.5, 320.1, 320.5, 311.1

[56] References Cited

U.S. PATENT DOCUMENTS

| | | | |
|---|---|---|---|
| 3,823,240 | 7/1974 | Sauli et al. | 514/391 |
| 4,097,578 | 6/1978 | Perronet et al. | 548/317.1 |
| 4,234,736 | 11/1980 | Bernauer et al. | 548/317.1 |
| 4,304,782 | 12/1981 | Dymont et al. | 548/321.1 X |
| 4,407,814 | 10/1983 | Bernauer et al. | 548/317.1 |
| 4,427,438 | 1/1984 | Nagano et al. | 548/317.1 |
| 4,473,393 | 10/1984 | Nagpal | 548/321.1 X |
| 4,482,739 | 11/1984 | Bernauer et al. | 564/54 |
| 4,749,403 | 6/1988 | Liebl et al. | 548/321.1 X |
| 4,859,228 | 8/1989 | Prisbylla | 548/321.1 X |
| 4,873,256 | 10/1989 | Coussediere et al. | 548/317.1 |
| 4,944,791 | 7/1990 | Schroder et al. | 548/321.1 X |
| 5,069,711 | 12/1991 | Fischer et al. | 548/317.1 X |

FOREIGN PATENT DOCUMENTS

| | | | |
|---|---|---|---|
| 0217893 | 6/1958 | Australia | 548/321.1 |
| 0017976 | 10/1980 | European Pat. Off. | 548/317.1 |
| 2102605 | 7/1971 | Germany | 548/321.1 |
| 48-87030 | 11/1973 | Japan | 548/317.1 |

OTHER PUBLICATIONS

Raynaud et al., J. Steriod Biochem., vol. 11, pp. 93–99 (1979).
Rao et al., J. Steriod Biochem., vol. 31, pp. 731–737 (1988).

Primary Examiner—Floyd D. Higel
Attorney, Agent, or Firm—Bierman and Muserlian

[57] ABSTRACT

A compound of the formula

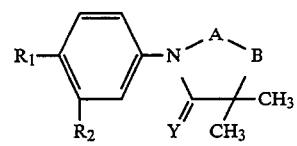

I wherein $R_1$ is —CN, —NO$_2$ or halogen, $R_2$ is —CF$_3$ or halogen, —A-B— is of

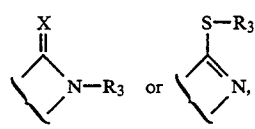

X is —O— or —S—, $R_3$ is hydrogen, alkyl, alkenyl or alkynyl of up to 12 carbon atoms, aryl and aralkyl of up to 12 carbon atoms, all optionally substituted by —OH, halogen, —SH, —CN, acyl and acyloxy of up to 7 carbon atoms, —aryl, —O—aryl, —O—aralkyl —S— aryl of up to 12 carbon atoms the aryl and aralkyl being optionally substituted by halogen, —CF$_3$, alkyl, alkoxy, alkenyl, alkenyloxy, alkynyl or alkynyloxy with the sulfur being optionally oxidized to sulfone or sulfoxide, free, esterified, amidified or salified carboxy, —NH$_2$, mono and dialkylamino and heterocyclic of 3 to 6 ring members and containing at least one heteroatom selected from the group consisting of oxygen, sulfur and nitrogen, the alkyl, alkenyl and alkynyl being optionally interrupted by at least one oxygen, nitrogen or sulfur optionally oxidized to sulfoxide or sulfone, trialkylsilyl with the alkyl having 1 to 6 carbon atoms and acyl and acyloxy of an organic carboxylic acid of 1 to 7 carbon atoms and Y is —O—, —S— or —NH—, except the compounds wherein —A-B— is

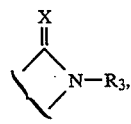

X is oxygen, $R_3$ is hydrogen and Y is oxygen or —NH—, $R_2$ is —CF$_3$ or halogen and $R_1$ is —NO$_2$ or halogen and their non-toxic, pharmaceutically acceptable acid addition salts.

20 Claims, No Drawings

PHENYLIMIDAZOLIDINES HAVING ANTIANDROGENIC ACTIVITY

PRIOR APPLICATION

This application is a continuation-in-part of U.S. Patent application Ser. No. 819,910, filed Jan. 9, 1992, now abandoned.

Japanese application No J 48087030 describes 3-phenyl-2-thiohydantoins useful for inhibiting the germination of certain plants. U.S. Pat. No. 4,097,578 describes imidazolidines different from formula I having antiandrogenic activity. Other pertinent art includes U.S. Pat. Nos. 3,823,240; No. 4,873,256; No. 4,407,814; No 4,482,739 and No. 4,234,736.

OBJECTS OF THE INVENTION

It is an object of the invention to provide the novel compounds of formula I and a novel process and novel intermediates for their preparation.

It is another object of the invention to provide novel anti-androgenic compositions and a novel method of inducing anti-androgenic activity in warm-blooded animals.

These and other objects and advantages of the invention will become obvious from the following detailed description.

THE INVENTION

The novel phenylimidazolidines of the invention have the formula

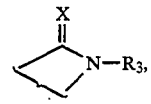

wherein $R_1$ is selected from the group consisting of —CN, —NO$_2$ and halogen, $R_2$ is —CF$_3$ or halogen, —A-B— is selected from the group consisting of

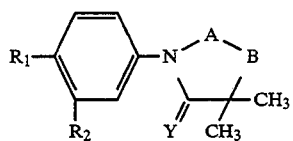

X is —O— or —S—, $R_3$ is selected from the group consisting of hydrogen, alkyl, alkenyl and alkynyl of up to 12 carbon atoms, aryl and aralkyl of up to 12 carbon atoms, all optionally substituted with at least one member of the group consisting of —OH, halogen, —SH, —CN, acyl and acyloxy of up to 7 carbon atoms, —aryl, —O—aryl, —O—aralkyl —S—aryl of up to 12carbon atoms, the aryl and aralkyl being optionally substituted with a member of the group consisting of halogen, —CF$_3$, alkyl, alkoxy, alkenyl, alkenyloxy, alkynyl and alkynyloxy with the sulfur being optionally oxidized to sulfone or sulfoxide, free, esterified, amidified or salified carboxy, —NH$_2$, mono and dialkylamino and heterocyclic of 3 to 6 ring members and containing at least one heteroatom selected from the group consisting of oxygen, sulfur and nitrogen, the alkyl, alkenyl and alkynyl being optionally interrupted with at least one member of the group consisting of oxygen, nitrogen and sulfur optionally oxidized to sulfoxide or sulfone, trialkylsilyl with the alkyl having 1 to 6 carbon atoms and acyl and acyloxy of an organic carboxylic acid of 1 to 7 carbon atoms and Y is —O—, —S— or —NH—, except the compounds wherein —A-B— is

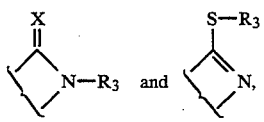

X is oxygen, $R_3$ is hydrogen and Y is oxygen or —NH—, $R_2$ is —CF$_3$ or halogen and $R_1$ is —NO$_2$ or halogen and their non-toxic, pharmaceutically acceptable acid addition salts.

The following examples are given for the values of $R_3$. Alkyl of up to 12 carbon atoms includes methyl, ethyl, propyl, isopropyl, butyl, isobutyl, sec.-butyl, tert.-butyl, pentyl, isopentyl, sec.-pentyl, tert.-pentyl, neopentyl, hexyl, isohexyl, sec.-hexyl, tert.-hexyl, heptyl, octyl, decyl, undecyl and dodecyl, branched or linear. Preferred are alkyl of 1 to 6 carbon atoms, especially methyl, ethyl, propyl and isopropyl, n-butyl, isobutyl, tert-butyl and branched or linear pentyl and hexyl.

Examples of alkenyl of up to 12 carbon atoms are vinyl, allyl, 1-propenyl, butenyl, pentenyl and hexenyl and preferably alkenyl of 2 to 4 carbon atoms and especially vinyl, allyl or butenyl. Examples of alkynyl of up to 12 carbon atoms are ethynyl, propargyl, butynyl, pentynyl and hexynyl and preferably 2 to 4 carbon atoms such as ethynyl and propargyl.

Examples of aryl are carbocyclic aryl such asphenyl and naphthyl, heterocyclic aryl of 5 to 6 ring members containing at least one heteroatom selected from the group consisting of oxygen, sulfur and nitrogen. Examples of 5 ring heteroaryls are furyl, thienyl, pyrrolyl, thiazolyl, oxazolyl, imidazolyl, thiadiazolyl, pyrazolyl and isoxazolyl. Examples of 6 ring heteroaryl are pyridyl, pyrimidinyl, pyridazinyl and pyrazinyl. Examples of condensed aryls are indolyl, benzofurannyl, benzothienyl and quinoleinyl. The preferred aryl is phenyl.

Examples of aralkyl include the alkyl recited above substituted with the aryl cited above. The preferred aralkyl are triphenylmethyl, phenethyl and benzyl. Examples of halogen are fluorine, chlorine, bromine and iodine but preferred are fluorine, chlorine and bromine. Examples of alkyl substituted with at least one halogen are fluoromethyl, chloromethyl, bromomethyl, iodomethyl, difluoromethyl, dichloromethyl, dibromomethyl and trifluoromethyl.

Examples of substituents for aryl and aralkyl are phenyl substituted by fluorine, —OCH$_3$ or —CF$_3$ in the p-position.

Examples of acyl are preferably those of up to 7 carbon atoms such as acetyl, propionyl, butyryl and benzoyl as well as valeryl, hexanoyl, acryloyl, crotonoyl, carbamoyl or formyl. The acyloxy may be derived for the same acids, especially acetyloxy and propionyloxy.

The esterified carboxy may be alkoxycarbonyl such as methoxycarbonyl, ethoxycarbonyl, propoxycarbonyl, butoxycarbonyl, tert.-butoxycarbonyl, cyclobutyloxy carbonyl, cyclopentyloxy carbonyl and cyclohexylocy carbonyl.

Examples of easily cleavable esters includes methoxymethyl, ethoxymethyl; acyloxyalkyl such as pivaloyloxymethyl, pivaloyloxyethyl, acetoxymethyl and acetoxyethel; alkoxycarbonyloxyalkyl such as methoxycarbonyloxymethyl, methoxycarbonyloxyethyl, isopropoxycarbonyloxymethyl and isopropoxycarbonyloxyethyl. Other esters are described in European Patent No. 0.034.536.

The amidified carboxy are of the type

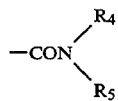

wherein R₄ and R₅ are individually selected from the group consisting of hydrogen and alkyl of 1 to 4carbon atoms such as methyl, ethyl, propyl, isopropyl, butyl, isobutyl, sec.-butyl and tert.-butyl.

Examples of the mono and dialkylamino are methylamino, ethylamino, dimethylamino, diethylamino and methylethylamino. The hetero-cyclic of 5 to 6 ring members optionally containing another heteroatom may be pyrrolyl, imidazolyl, pyridyl, pyrazinyl, pyrimidyl, indolyl, piperidino, morpholino and piperazinyl, preferably piperidino or morpholino.

Examples of salts of salified carboxy are sodium, potassium, lithium, calcium, magnesium, ammonium and organic bases such as methylamine, propylamine, trimethylamine, diethylamine and triethylamine. Sodium salt is preferred.

The alkylamino and dialkylamino are preferably alkyl of 1 to 4 carbon atoms such as methylamino, ethylamino, propylamino, isopropylamino, dimethylamino, diethylamino and ethylmethylamino.

Examples of the heterocyclics containing at least one heteroatom are saturated monocyclics such as oxirannyl, oxolannyl, dioxolannyl, imidazolidinyl, pyrazolidinyl, piperidyl, piperazinyl and morpholinyl.

The alkyl, alkenyl and alkynyl may be optionally interrupted by one or more sulfur, oxygen or nitrogen heteroatoms. Examples are alkoxyalkyl such as methoxymethyl, methoxyethyl, methoxypropyl or methoxybutyl or alkoxy alkoxyalkyl such as methoxyethoxymethyl.

Examples of trialkylsilyl groups are trimethylsilyl, triethylsilyl and (1,1-dimethylethyl) dimethylsilyl.

When the products of formula I contain a salifiable amino group, the acid addition salts of non-toxic, pharmaceutically acceptable acids may be formed. Examples of said acids are inorganic acids such as nitric acid, hydrochloric acid, sulfuric acid and phosphoric acid and organic acids such as formic acid, acetic acid, propionic acid, benzoic acid and methane sulfonic acid.

Among the preferred compounds of formula I are those wherein Y is oxygen except for the compounds wherein —A–B— is

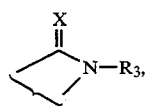

X is oxygen, R₃ is hydrogen, R₂ is —CF₃ or halogen and R₁ is —NO₂ or halogen. Other preferred compounds of formula I are those wherein —A–B— is

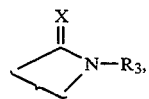

X is sulfur and R₃ has the above definition, those wherein R₃ is hydrogen or alkyl of 1 to 4 carbon atoms optionally substituted with —OH or methoxy, those wherein R₁ is cyano or halogen, preferably chlorine and those wherein —A–B— is

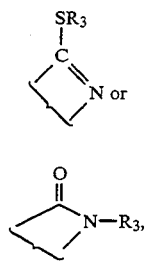

and R₃ is optionally substituted alkyl or alkenyl of up to 6 carbon atoms and optionally interrupted by oxygen or optionally oxidized sulfur or optionally substituted aralkyl, acyl or trialkylsilyl.

Other preferred examples of the invention are those in which R₃ is alkyl of up to 6 carbon atoms optionally substituted by at least one member of the group consisting of halogen, free or esterified hydroxy or carboxy, heterocyl, O-aralkyl or S-aryl in which the aryl radical is optionally substituted by at least one halogen or alkoxy and the sulfur atom is optionally oxidized in the form of the sulfoxide or sulfone and quite particularly those in which R₃ is alkyl of 2 to 4 carbon atoms substituted by a member of the group consisting of chlorine, ethoxycarbonyl, terbutoxycarbonyl, cyclopentyloxycarbonyl, 4-fluorophenylthio optionally oxidized in the form of the sulfoxide or sulfone, morpholino, phenylmethoxy, triphenylmethoxy and methylsulfonyloxy.

Other preferred compounds of formula I are those wherein R₃ is acetyl or benzoyl or (1,1-dimethylethyl) dimethylsilyl, those wherein R₁ is nitro and R₃ is alkyl or alkenyl of up to 4 carbon atoms optionally substituted with esterified or salified or free carboxy and those of the formula

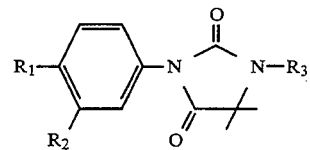

in which R₁, R₂ and R₃ have the above meaning with the exception of the products in which R₁ is nitro, R₂ is trifluoromethyl and R₃ is hydrogen.

Examples of specific preferred compounds of formula I are 4-(5-oxo-2-thioxo-3,4,4-trimethyl-1-imidazolidinyl)-2-(trifluoromethyl)-benzonitrile, 4-(4,4-dimethyl-5-oxo-2-thioxo-1-imidazolidinyl)-2-(trifluoromethyl)-benzonitrile, 4-[4,4-dimethyl 3-(2-hydroxyethyl)-5-oxo-2-thioxo-1-imidazolidinyl]-2-(trifluoromethyl) benzonitrile, 3-(3,4-dichlorophenyl)-2-thioxo-1,5,5-trimethyl-4-imidazolidinone, 1-(4-nitro-3-(trifluoromethyl)-phenyl)-3,4,4-trimethyl-2,5-imidazolidinedione, 4-[[4,5-dihydro-4,4-dimethyl-5-oxo-2-ben-zyl-thio]-1H-imidzao-1-yl]-2-(trifluoromethyl) benzonitrile, 4-[4,4-dimethyl 3-(2-hydroxyethyl) 5-oxo 2-thioxo 1-imidazolidinyl] 2-(trifluoromethyl) benzonitrile, 4-(4,4-dimethyl 2,5-dioxo 3-(4-hydroxybutyl) 1-imidazolidinyl) 2-(trifluoromethyl) benzonitrile, 4-(4,4-dimethyl 3-(4-hydroxybutyl) 5-oxo 2-thioxo 1-imidazolidinyl) 2-(trifluoromethyl) benzonitrile and 3-(4-cyano 3-(trifluoromethyl) phenyl) 5,5-dimethyl 2,4-dioxo 1-imidazolidinebutanoic acid.

The process of the invention for the preparation of a compound of formula I comprises either reacting a compound of the formula

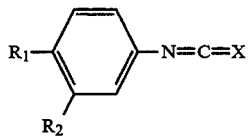   II wherein $R_1$, $R_2$ and X have the above definitions with a compound of the formula

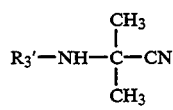   III in the presence of a tertiary base wherein $R'_3$ has the definition of $R_3$ with reactive group optionally protected and if $R_1$ is $-NO_2$ or halogen, $R_2$ is halogen or $-CF_3$ and X is oxygen, $R'_3$ is not hydrogen to obtain a compound of the formula

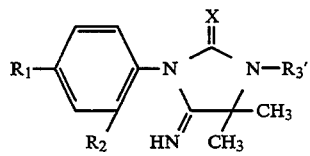   IV wherein $R_1$, $R_2$, X and $R'_3$ have the above definitions and optionally subjecting the latter to one or more of the following reactions in any order:
a) reaction to eliminate the optional protective groups of $R'_3$
b) reaction of hydrolysis of C=NH to a ketone function or transformation of C=S to C=O
c) transformation reaction of C=O to C=S
d) and reacting the products of formula IV wherein $R'_3$ is hydrogen and after hydrolysis of C=NH to a ketone with a compound of the formula $R''_3$-Hal where Hal is a halogen and $R''_3$ is $R'_3$ except hydrogen to obtain a compound of formula I wherein $-A-B-$ is

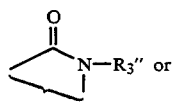 or

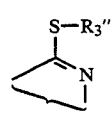

and optionally reacting the latter to eliminate the protective group of $R''_3$ or reacting the same with an esterification, salification or amidification agent or reacting a compound of the formula

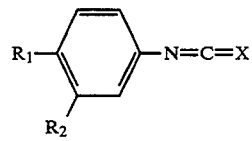   II in which $R_1$, $R_2$ and X have the above meaning in the presence of a tertiary base with a product of the formula

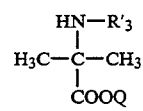   III in which $R'_3$ has the above meaning and Q is either an alkali metal for example sodium or alkyl of 1 to 6 carbon atoms to obtain a product of the formula

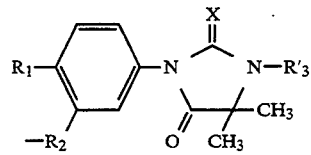   IVa in which X, $R_1$, $R_2$ and $R'_3$ have the above meaning which if desired is subjected to any one or more of the following reactions in any order:
a) elimination reaction of the optional protective groups that can be carried by $R'_3$;
b) conversion reaction of the >C=O group or groups into the >C=S or if appropriate of >C=S into >C=O;
c) the action on the products of formula IVa in which $R'_3$ is hydrogen of a reagent of formula Hal—$R''_3$ in which $R''_3$ has the values of $R'_3$ with the exception of hydrogen and Hal is halogen to obtain the products of formula I in which $-A-B-$ is

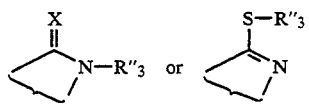

in which $R''_3$ has the above meaning, then, if desired, the action of these products of an elimination agent of the optional protective groups that can be carried by $R''_3$ or if appropriate, the action of an esterification, amidification or salification agent, or reacting a reagent of the formula $R''_3$—Hal as defined above with a compound of the formula

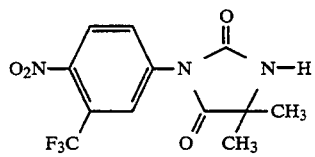   IV' to obtain a compound of the formula

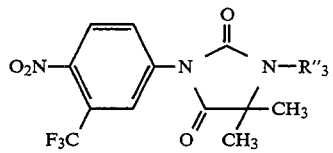

and optionally subjecting the latter to one or more of the following reactions:

a) elimination reaction of optional protective groups of R″₃ and then to reaction with an esterification, salification or amidification reagent
b) reaction of transformation of C=O to C=S.

The reaction of the products of formula II with the products of formula III is preferably effected in an organic solvent such as tetrahydrofuran or dichloroethane or ethyl ether or isopropyl ether in the presence of a tertiary base such as pyridine or methylethyl pyridine.

The optional reactive functional groups of R₃ which are optionally protected in compounds of formula III, IVa or IV″ are —OH or amino which are protected by the usual protective groups. Examples of such protective groups for —NH₂ are tert.-butyl, tert.-amyl, trichloroacetyl, chloroacetyl, benzhydryl, trityl, formyl and benzyloxycarbonyl. Examples of hydroxy protective groups are formyl, chloroacetyl, tetrahydropyrannyl, trimethylsilyl and tert.-butyldimethylsilyl.

The above list of protective groups is not intended to be exhaustive and any protective group known, for example, in peptide chemistry may be used. Other known protective groups are described in French Patent No. 2,499,995 which is incorporated herein by reference. The optional reactions to eliminate groups are indicated in the said patent and the preferred method of elimination is acid hydrolysis with hydrochloric acid, benzene sulfonic acid, p-toluene sulfonic acid, formic acid or trifluoroacetic acid, preferably hydrochloric acid.

The optional reaction of hydrolysis of C=NH to C=O is preferably effected with an acid suchas refluxing aqueous hydrochloric acid. When the hydrolysis of C=NH into a C=O is effected with a molecule also containing C=S, the latter may be transformed in C=O group. The free hydroxy optionally contained in R₃ may also be transformed into —SH.

The transformation of the group C=O into C=S is effected with a Lawesson reagent of the formula

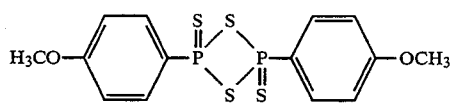

which is a commercial product sold by Fluka for example and is described in Bull. Soc. Chim. Belg., Vol 87 No. 3 (1987), p. 229. When two C=O groups are to be changed to C=S, the reaction is effected in an excess of the Lawesson reagent. The same is used also when the molecule contains both C=S and C=O and it is desired to change the C=O to C=S.

On the contrary, when part of the molecule contain two C=O and it is desired to obtain a product with only one C=S, a deficiency of the Lawesson reagent is used to obtain a mixture of 3 products, each of two products with a C=O and C=S and one containing two C=S.

The said products can be separated by known methods such as chromatography.

The reaction of the compounds of formulae IV, IVA or IV′ with a compound of the formula R″₃—Hal is effected in the presence of a strong base such as sodium hydride or potassium hydride in a phase transfer reaction in the presence of quaternary ammonium salts such as tert.-butyl ammonium. The protective groups of R″₃ may be those discussed above for R₃. The reaction to eliminate the protective groups are as discussed above. For example, a tert-butyl dimethylsilyl group may be removed by hydrochloric acid as described in the examples infra.

The optional esterification of the compounds of formula I wherein R″₃ is free —OH is effected under the classical conditions using for example an acid or a functional derivative thereof such as its anhydride like acetic acid anhydride in the presence of a base such as pyridine. The optional esterification or salification of the compounds of formula I wherein R″₃ is —COOH may be effected by known methods.

The optional amidification of the compounds of formula I wherein R″₃ is —COOH is effected also under classical conditions with primary or secondary amine with a functional derivative of —COOH such as a symetrical or mixed anhydride thereof.

The process of the invention to prepare compounds of the formula

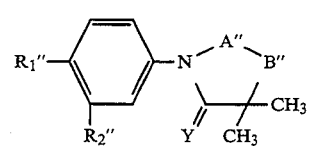

wherein R″₁, R″₂ and —A″-B″— have the definitions of R₁, R₂ and —A-B— except when —A″-B″— is

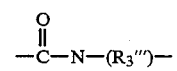

and R‴₃, is hydrogen or alkyl of 1 to 7 carbon atoms and Y is oxygen, R″₁ is —CN comprises reacting a compound of the formula

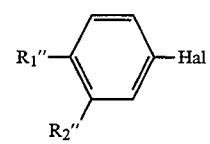

wherein R″₁ and R″₂ have the above definitions and Hal is halogen with a compound of the formula

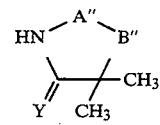

wherein —A″-B″— and Y have the above definitions in the presence of a catalyst and optionally a solvent. In the compounds of formula V, the halogen is preferably chlorine but may be iodine or bromine.

The role of the catalyst is obviously to trap the hydrogen halide as it forms and to facilitate the condensation reaction of the compounds of formulae V and VI to form the desired product. The catalyst is preferably a metal in its native form or its oxide or salt form or it may be a base. When the catalyst is a metal, it is preferably copper or nickel and the metallic salts are preferably the chloride or acetate. When the catalyst is a base, it is preferably sodium hydroxide or potassium hydroxide and dimethylsulfoxide may be added to the reaction medium.

The catalyst of the process may be selected from cuprous oxide, cupric oxide, metallic copper or a base such as sodium hydroxide or potassium hydroxide, preferably cuprous oxide in powdered form. The solvent used preferably is a high boiling point ether such as phenyl oxide, diglyme, triglyme and dimethylsulfoxide but also useful are high boiling point oils such as paraffin or vaseline. Preferably, the process is effected in another solvent such as phenyl oxide, diglyme, triglyme or dimethylsulfoxide, most preferably in phenyl oxide or triglyme.

The process may be effected at atmospheric pressure or under pressure at temperatures above 100° C., preferably above 150° C. for more than two hours. The reaction is preferably effected with cuprous oxide in triglyme at temperatures of 200° C. or higher for more than three hours.

The novel anti-androgenic compositions of the invention are comprised of an anti-androgenically effective amount of at least one compound of formula I and its non-toxic, pharmaceutically acceptable acid addition salts and an inert pharmaceutical carrier. The compositions may be in the form of tablets, dragees, capsules, syrups, suppositories, creams, pomades, lotions or injectable solutions prepared in the usual manner.

Examples of suitable excipients are aqueous or non-aqueous vehicles, arabic gum, lactose, starch, magnesium stearate, cocoa butter, fatty bodies of animal or vegetable origin, paraffinic derivatives, glycols, diverse wetting agents, dispersants or emulsifiers and preservatives.

The compositions inhibit the effect of androgens on peripherical receptors and have an anti-androgenic activity useful for therapy in adults without the certain effects of a chemical castration. The compositions are useful for the treatment of adenomas and neoplasies of the prostate as well as benign hypertrophia of the prostate as well as the treatment of benign or malignant tumors of cells containing androgen receptors. They are particularly useful for the treatment of breast, brain, skin and ovarian cancer and bladder, lymphatic system, liver and kidney cancers. They are equally useful for the treatment of hirsutism, acne, seborrhea, androgenic alopecia and hyperpilosity and in the veterinary field.

The compositions of the invention are useful in dermatology and can contain another ingredient such as an antibiotic such as derivatives of retinoids for the treatment of acne, or with a 5α-reductase inhibitor such as (5=, 17β)-1,1-dimethylethyl 3-oxo 4-aza-Δ¹-androstene-17 carboxamide (or Finasteride Merck, 11th ed.) or azelaic acid or a blocking agent of androgen receptors for the treatment of acne, alopecia or hirsutism, or with a product stimulating the growth of hair such as Minoxidil for the treatment of alopecia. The compositions can also be used in the veterinary domain and in the form of radioactive products, can also be used in diagnostics as specific labels for the androgen receptors. As radioactive products, the products labelled with tritium, with carbon 14 or also with iodine 125 can be used.

The novel method of the invention for inducing anti-androgenic activity in warm-blooded animals, including humans, comprises administering to warm-blooded animals an anti-androgenically effective amount of at least one compound of formula I and its non-toxic, pharmaceutically acceptable acid addition salts. The compounds may be administered parenterally, buccally, perlingually, rectally or topically and the usual daily dose is 0.133 to 6.66 mg/kg depending on the condition treated, the specific compound and the method of administration.

The starting compounds of formula II may be prepared by reacting phosgene when X is oxygen or thiophosgene when X is sulfur with an amine of the formula

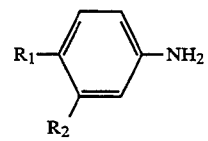

A

A product of this type is described in French Patent No. 2,329,276. The amines of formula A are described in EP Patent No. 0,002,892 and French Patent No. 2,142,804.

The products of formula III or III' are known or can be prepared from the corresponding cyanhydrin by the process of J. Am. Chem. Soc., Vol 75 (1953), p. 4841. The compounds of formula III wherein R'₃ is other than hydrogen may be obtained by reacting a compound of the formula R"₃ Hal with 2-cyano-2-amino-propane under the conditions described above for reacting the said halide with the compounds of formula IV. An example is described by Jilek et al, Collect. Czech. Chem. Comm., Vol 54(8) (1989), p. 2248. The products of formula IV' are described in French Patent No. 2,329,276.

The compounds of formulae V and VI are commercially available known compounds and can be prepared by known methods.

The preparation of the compounds of formula VI are described in the following publications: Zhur Preklad Khim., Vol. 28 (1955), p. 969-75 (CA, Vol. 50 (1956), p 4881a); Tetrahedron, Vol. 43 (1987), p. 1753; J. Org. Chem., Vol. 52 (1987), p. 2407; Zh. Org. Khim., Vol. 21 (1985), p. 2006; J. Fluor. Chem., Vol. 17 (1981), p. 345; German Patent No. 637,318, European Patent No. 0,130,875 and Japanese Patent No. 81-121,525.

The products of formula VI which are derivatives of hydantoin are largely used and are known in the literature such as J. Pharm. Pharmacal., 67, Vol. 19(4) (1967), p. 209-16; J. Chem. Soc., Vol. 74(2) (1972), p. 219-221; Khim. Farm. Zh., Vol. 67(1)(5), p. 51-2; German Patent No. 2,217,914; European Patent No. 0,091,596 and J. Chem. Soc. Perkin. Trans. 1, Vol. 74(2), p. 48 and 219-221.

The novel intermediates of the invention are the compounds of the formula

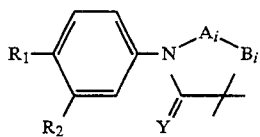

wherein $R_1$, $R_2$ and Y have the above definitions and —Ai–Bi— is

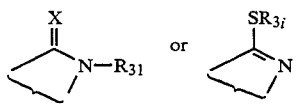

wherein X is oxygen or sulfur and $R_{3i}$ is $R_3$ with the reactive groups protected among which are —OH or —$NH_2$ protected as above for $R_3$.

In the following examples, there are described several preferred embodiments to illustrate the invention. However, it should be understood that the invention is not intended to be limited to the specific embodiments.

EXAMPLE 1

1-(4-nitro-3-trifluoromethyl-phenyl)-3,4,4-trimethyl-2,5-imidazolidinedione

A solution of 3.17 g of 1-(3-trifluoromethyl-4-nitro-phenyl)-4,4-dimethyl-imidazoline-2,5-dione (French Patent No. 2,329,276) and 32 ml of dimethylformamide were added at 23° C. to 26° C. to a 50% suspension of 492 mg of sodium hydride in oil and 3 ml of dimethylformamide and after stirring for 15 minutes, a solution of 0.7 ml of methyl iodide in 2 ml of dimethylformamide was added. The mixture was stirred for 25 minutes at 24° C. to 28° C. and was then poured into 200 g of a 1—1 water-ice mixture. The mixture was extracted with ether and the organic phase was washed with saturated aqueous sodium chloride, dried, filtered and evaporated to dryness under reduced pressure to obtain 3.6 g of the desired product melting at 116° C. An analytical sample was crystallized from isopropyl alcohol to obtain 2.73 g of the product melting at 116° C.

| Analysis: $C_{13}H_{12}F_3N_3O_4$; molecular weight = 331.25 | | | | |
|---|---|---|---|---|
| | % C | % H | % F | % N |
| Calculated: | 47.14 | 3.65 | 17.20 | 12.68 |
| Found: | 47.0 | 3.5 | 17.1 | 12.5 |

| IR Spectrum ($CHCl_3$): | |
|---|---|
| C=O | 1780, 1727 cm$^{-1}$ |
| aromatics | 1615, 1596, 1497 cm$^{-1}$ |
| $NO_2$ | 1545, 1357 cm$^{-1}$ |

EXAMPLE 2

5,5-dimethyl-1-ethyl-3-(4-nitro-3-trifluoromethyl-phenyl)-2,4-imidazolidinedione Using the procedure of Example 1, 1 g of 1-(3-trifluoromethyl-4-nitro-phenyl)-4,4-dimethyl imidazoline-2,5-dione prepared as in French Patent No. 2,329,276 was reacted with 0.37ml of ethyl iodide and a 50% suspension of 166 mg of sodium hydride in oil to obtain 1.19 g of the desired product melting at 110° C. to 111° C. which was crystallized from isopropanolto obtain 934 mg of the product melting at 110° C. to 111° C.

| Analysis: $C_{14}H_{14}F_3N_3O_4$; molecular weight = 345.28 | | | | |
|---|---|---|---|---|
| | % C | % H | % F | % N |
| Calculated: | 48.70 | 4.09 | 16.51 | 12.17 |
| Found: | 48.6 | 4.0 | 16.8 | 12.1 |

| IR Spectrum ($CHCl_3$): | |
|---|---|
| C=O | 1777, 1724 cm$^{-1}$ |
| $NO_2$ | 1545, 1356 cm$^{-1}$ |
| aromatics | 1614, 1596, 1497 cm$^{-1}$ |

EXAMPLE 3

5,5-dimethyl-3-(4-nitro-3-trifluoromethyl-phenyl)-1-propyl-2,4-imidazolidinedione Using the procedure of Example 1, 1 g of 1-(3-trifluoromethyl-4-nitro-phenyl)-4,4-dimethyl imidazoline-2,5-dione was reacted with 0.35 ml of 1-iodopropane and a 50% suspension of 155mg of sodium hydride in oil to obtain after chromatography on silica with an eluant of acetone-methylene chloride (1–99), 3.087 g of raw product melting at 102° C. The product was crystallized from isopropanol to obtain 945 mg of the desired product melting at 102° C.

| Analysis: $C_{15}H_{16}F_3N_3O_4$; molecular weight = 359.31 | | | | |
|---|---|---|---|---|
| | % C | % H | % F | % N |
| Calculated: | 50.14 | 4.49 | 15.86 | 11.69 |
| Found: | 50.1 | 4.4 | 15.9 | 11.5 |

| IR Spectrum ($CHCl_3$): | |
|---|---|
| C=O | 1778, 1724 cm$^{-1}$ |
| $NO_2$ | 1544, 1358 cm$^{-1}$ |
| aromatics | 1615, 1596, 1497 cm$^{-1}$ |

EXAMPLE 4

5,5-dimethyl-1-isopropyl-3-(4-nitor-3-trifluoromethyl-phenyl)-2,4-imidazolidinedione Using the procedure of Example 1, 1 g of 1-(3-trifluoromethyl-4-nitro-phenyl)-4,4-dimethyl imidazoline-2,5-dione was reacted with 0.4 ml of 2-iodopropane and a 50% suspension of 166 mg of sodium hydride in oil for 18 hours at 50° C. to obtain after chromatography over silica (eluant methylene chloride-acetone 99–1), 685 mg of product melting at 130° C. which after crystallization from isopropanol yielded 661 of the desired product melting at 130° C.

| Analysis: $C_{15}H_{16}N_3F_3O_4$; molecular weight = 359.31 | | | | |
|---|---|---|---|---|
| | % C | % H | % F | % N |
| Calculated: | 50.14 | 4.49 | 15.86 | 11.69 |
| Found: | 50.1 | 4.4 | 16.2 | 11.6 |

| IR Spectrum ($CHCl_3$): | |
|---|---|
| C=O | 1779, 1771, 1723 cm$^{-1}$ |

-continued

| IR Spectrum (CHCl₃): | |
|---|---|
| NO₂ | 1544, 1361 cm⁻¹ |
| aromatics | 1615, 1596, 1497 cm⁻¹ |

EXAMPLE 5

5,5-dimethyl-3-(4-nitro-3-trifluoromethyl-phenyl)-1-(2-propenyl)-2,4-imidazolidinedione Using the procedure of Example 1, 1 g of 1-(3-trifluoromethyl-4-nitro-(henyl)-4,4-dimethyl imidazoline-2,5-dione was reacted with 0.35 ml of allyl bromide and a 50% suspension of 166 mg of sodium hydride in oil to obtain after chromatography over silica (eluant—methylene chloride-acetone (99–1)) 1.10 g of product which after crystallization from isopropanol yielded 1.01 g of the desired product melting at 105° C.

| Analysis: $C_{15}H_{14}F_3N_3O_4$; molecular weight = 357.29 | | | | |
|---|---|---|---|---|
| | % C | % H | % F | % N |
| Calculated: | 50.42 | 3.95 | 15.95 | 11.76 |
| Found: | 50.4 | 3.8 | 15.8 | 11.7 |

| IR Spectrum (CHCl₃): | |
|---|---|
| C=O | 1779, 1724 cm⁻¹ |
| NO₂ | 1545, 1358 cm⁻¹ |
| aromatics | 1615, 1596, 1497 cm⁻¹ |
| CH=CH₂ | 1643, 930 cm⁻¹ |

EXAMPLE 6

5,5-dimethyl-3-(3-trifluoromethyl-4-nitro-phenyl)-1-benzyl-2,4-imidazolidinedione Using the procedure of Example 1, 2 g of 1-(3-trifluoromethyl-4-nitro-phenyl)-4,4-dimethyl imidazolidine-2,5-dione was reacted with 0.71 ml of benzyl bromide and a 50% suspension of 332 mg of sodium hydride in oil to obtain after chromatography on silica and elution with 99–1 methylene chloride-acetone 2.375 g of the desired product which as crystallized from isopropanol to obtain 2.165 g of product melting at 99° C.

| Analysis: $C_{19}H_{16}N_3F_3O_4$; molecular weight = 407.3 | | | | |
|---|---|---|---|---|
| | % C | % H | % F | % N |
| Calculated: | 56.02 | 3.96 | 10.31 | 14.00 |
| Found: | 56.1 | 3.8 | 10.2 | 13.9 |

| IR Spectrum (CHCl₃): | |
|---|---|
| C=O | 1799, 1723 cm⁻¹ |
| aromatics | 1608 cm⁻¹ |
| + | 1594 cm⁻¹ (m) |
| NO₂ | 1545 cm⁻¹ (F) |
| | 1497 cm⁻¹ |

EXAMPLE 7

4-(4,4-dimethyl-5-imino-2-oxo-1-imidazolidinyl)-2-trifluoromethylbenzonitrile

A solution of 10 g of 4-cyano-3-trifluoromethyl-aniline (described in European Paten No. 0,002,892) in 30 ml of ethyl acetate was added at 0 to 5° C. to 33.6 ml of a toluene solution of 1.93 M/l of phosgene and after stirring at 0 to 5° C. for 30 minutes, the temperature was raised to 25° C. The mixture was distilled while introducing fresh toluene maintaining to constant level for compensate the distilled volume of toluene until a temperature of about 110° C. was reached. The mixture was held at reflux until the disengagement of hydrogen chloride ceased (4 ½ hours). The temperature returned to room temperature and the white solid was dried over sodium sulfate and was rinsed with toluene 3 times. The organic phase was evaporated to dryness under reduced pressure, heated at 60° C. for one hour and then cooled under argon to obtain 11.6 g of 4-isocyanate of 2-trifluoromethyl-benzonitrile.

| IR Spectrum: | |
|---|---|
| —NC=O | 2268 cm⁻¹ |
| —CN | 2233 cm⁻¹ |

A solution of 6.6 g of 4-isocyanate of 2-trifluoromethyl-benzonitrile in 10 ml of dichloroethane was added at 5° C. to a solution of 2.63 g of 2-amino-2-cyano-propane and 36 ml of dichloroethane and 0.9 ml of triethylamine and after stirring 16 hours at room temperature, the mixture was evaporated to dryness. The 7.7 g of residue were chromatographed on silica and eluted with a 85–15 methylene chloride-acetone mixture to obtain 3.54 g of the desired product melting at 228° C. An analytical sample was prepared by crystallizing 300 mg from isopropanol to obtain 267 mg of the product melting at 228° C.

| Analysis: $C_{13}H_{11}F_3N_4O$; molecular weight = 296.25 | | | | |
|---|---|---|---|---|
| | % C | % H | % F | % N |
| Calculated: | 52.71 | 3.74 | 19.24 | 18.91 |
| Found: | 52.7 | 3.6 | 19.1 | 18.6 |

| IR Spectrum (Nujol): | |
|---|---|
| NH/OH | 3340, 3290 cm⁻¹ |
| CN | 2240 cm⁻¹ |
| C=O | 1760 cm⁻¹ |
| C=N | 1655 cm⁻¹ |
| aromatics | 1606, 1570, 1502 cm⁻¹ |

EXAMPLE 8

4-(4,4-dimethyl-2,5-dioxo-1-imidazolidinyl)-2-trifluoromethylbenzonitrile

A solution of 2.76 g of the product of Example 7 and 60 ml of 0.5 hydrochloric acid was refluxed for 35 minutes and was poured into 100 g of water and ice. The mixture was extracted with ethyl acetate and the organic phase was washed with water, dried and evaporated to dryness under reduced pressure to obtain 2.70 g of the desired product melting at 210° C. An analytical sample was obtained by crystallizing 440 mg of product from isopropanol to obtain 383 mg of product melting at 210° C. to 211° C.

| Analysis: $C_{13}H_{10}F_3N_3O_2$; molecular weight = 297.24 | | | | |
|---|---|---|---|---|
| | % C | % H | % F | % N |
| Calculated: | 52.53 | 3.39 | 19.17 | 14.14 |

-continued

| Analysis: $C_{13}H_{10}F_3N_3O_2$; molecular weight = 297.24 | | | | |
|---|---|---|---|---|
| | % C | % H | % F | % N |
| Found: | 52.4 | 3.2 | 19.4 | 13.9 |

| IR Spectrum (CHCl₃): | |
|---|---|
| CN | 2245 cm$^{-1}$ |
| C=O | 1788, 1722 cm$^{-1}$ |
| aromatics | 1610, 1572, 1502 cm$^{-1}$ |
| NH (max) | 3340 cm$^{-1}$ |

EXAMPLE 9

3-(4-cyano-3-trifluoromethyl-phenyl)-5,5-dimethyl-2,4-dioxo-1-imidazolidine acetic acid A solution of 600 mg of the product of Example 8 in 6 ml of dimethylformamide was added with stirring over 15 minutes to a suspension of a 50% suspension of 210 mg of sodium hydride in oil in 3 ml of dimethylformamide and after the addition of 290 mg of bromoacetic acid, the mixture was stirred for 16 hours at room temperature. After another 105 mg of sodium hydride were added, 145 mg of bromoacetic acid were added to the mixture which was stirred for 30 minutes and then poured into a mixture of 50 ml of water and 5 ml of 2N hydrochloric acid. The mixture was extracted with ether and the organic phase was washed with saturated aqueous sodium chloride, dried, filtered and evaporated to dryness under reduced pressure. The 1.22 g of residue were chromatographed on silica and eluted with a 90-10-0.5 methylene chloride-methanol-acetic acid mixture to obtain 367 mg of the desired product.

| IR Spectrum: | |
|---|---|
| CN | 2238 cm$^{-1}$ |
| C=O hydantoin & acid | 1784, 1725, 1710 cm$^{-1}$ |
| aromatic | 1616, 1580, 1508 cm$^{-1}$ |

| Ultra-violet Spectrum: | | |
|---|---|---|
| ETOH - 0.1N HCl | max 258 nm | $\epsilon$ = 13,300 |
| | inflex 277 nm | $\epsilon$ = 5,000 |
| | inflex 285 nm | $\epsilon$ = 2,600 |
| ETOH 0.1N NaOH | max 287 nm | $\epsilon$ = 19,100 |
| | max 342 nm | $\epsilon$ = 1,900 |

EXAMPLE 10

Ethyl3-(4-cyano-3-trifluoromethyl-phenyl)-5,5-dimethyl-2,4-dioxo-1-imidazolidine-acetate A solution of 600 mg of the product of Example 8 in6 ml of dimethylformamide was added to a 50% suspension of 100 mg of sodium hydride in oil and 3 ml of dimethylformamide and after stirring for 15 minutes, 0.25 ml of ethyl bromoacetate was slowly added at less than 30° C. The mixture was stirred for 30 minutes and then was poured into 50 g of a 1—1 ice-water mixture. 0.5 g of monopotassium phosphate was added and the mixture was extracted with ether. The organic phase was washed with water, dried and evaporated to dryness to obtain 1.1 g of residue which was chromatographed on silica and eluted with 97-3 methylene chloride-acetone to obtain 709 mg of the desired product melting at 152° C. An analytical sample was prepared by crystallization from isopropanol to obtain 667 mg of the desired product melting at 152° C.

| Analysis: $C_{17}H_{16}N_3F_3O_4$; molecular weight = 383.33 | | | | |
|---|---|---|---|---|
| | % C | % H | % F | % N |
| Calculated: | 53.21 | 4.21 | 14.83 | 10.96 |
| Found: | 53.3 | 4.0 | 14.9 | 10.8 |

| IR Spectrum (CHCl₃): | |
|---|---|
| CN | 2225 cm$^{-1}$ |
| imidazolidine | 1786, 1729 cm$^{-1}$ |
| COOEt | 1751 cm$^{-1}$ |
| aromatics | 1616, 1572, 1505 cm$^{-1}$ |

EXAMPLE 11

4-(5-imino-2-thioxo-3,4,4-trimethyl-1-imidazolidinyl)-2-trifluoromethyl-benzonitrile 2.23 of 1-trifluoromethyl-4-amino-benzonitrile (described in European Patent No. 0,002,892)were slowly added to a solution of 22 ml of distilled water and 1 ml of thiophosgene and after stirring for one hour, the mixture was extracted with chloroform. The organic phase was washed with aqueous sodium chloride, dried and evaporated to dryness under reduced pressure to obtain 3 g of isocyanate product which as used as is.

A mixture of the 3 g of product, 1.33 ml of 2-methylamino-2-cyano-propane, 23 ml of tetrahydrofuran and 0.23 ml of triethylamine was refluxed for 40 minutes and was evaporated to dryness. The 3.07 g of residue were chromatographed on silica and eluted with a 1—1 cyclohexane-ethyl acetate mixture and then a 95-5 methylene chloride-acetone mixture to obtain 2.83 g of product which was crystallized from isopropanol to obtain 2.63 g of the desired product melting at 173° C. to 174° C.

| Analysis: $C_{14}H_{13}F_3N_4S$; molecular weight = 326.35 | | | | | |
|---|---|---|---|---|---|
| | % C | % H | % F | % N | % S |
| Calculated: | 51.53 | 4.01 | 17.17 | 17.46 | 9.82 |
| Found: | 51.7 | 3.9 | 17.2 | 17.2 | 9.9 |

| IR Spectrum: | |
|---|---|
| C=NH | 3308, 1679 cm$^{-1}$ |
| C=S + aromatics | 1608, 1575, 1505, 1488 cm$^{-1}$ |
| CN | 2230 cm$^{-1}$ |
| CF₃ | 1185 cm$^{-1}$ |

EXAMPLE 12

4-(5-oxo-2-thioxo-3,4,4-trimethyl-1-imidazolidinyl)-2-trifluoromethyl-benzonitrile A mixture of 2.21 g of the product of Example 11and 44 ml of 0.5 N hydrochloric acid was refluxed with stirring for one hour and was then poured into 200 g of an ice-water (1—1) mixture. The mixture was extracted with methylene chloride and the organic phase was washed with saturated aqueous sodium chloride, dried and evaporated to dryness. The residue was chromatographed on silica and eluted with a 1—1cyclohexane-ethyl acetate mixture to obtain 2.1 g of product melting at 171° C. which was crystallized from isopropanol to obtain 1.99 g of the desired product melting at 171° C.

| Analysis: $C_{14}H_{12}F_3N_3OS$; molecular weight = 327.33 | | | | | |
|---|---|---|---|---|---|
| | % C | % H | % F | % N | % S |
| Calculated: | 51.37 | 3.69 | 12.84 | 17.41 | 9.79 |
| Found: | 51.4 | 3.5 | 12.7 | 17.6 | 10.79 |

| IR Spectrum (CHCl₃): | |
|---|---|
| C=O | 1761, 1756 cm⁻¹ |
| aromatics | 1610, 1578, 1505 cm⁻¹ |
| CN | 2230 cm⁻¹ |
| CF₃ | 1178 cm⁻¹ |

EXAMPLE 13

4-(2,5-dithioxo-3,4,4-trimethyl-1-imidazolidinyl)-2-trifluoromethyl-benzonitrile A mixture of 839 mg of the product of Example 12, 518 mg of Lawesson reagent and 4.7 ml of toluene was refluxed for 24 hours and was then evaporated to dryness under reduced pressure. The 1.36 g of residue were chromatographed on silica and eluted with a 99-1 methylene chloride-ethyl acetate mixture and then an 85-15 cyclohexane-ethylacetate mixture to obtain 783 mg of product which was crystallized from isopropanol to obtain 690 mg of the desired product melting at 211° C. to 212° C.

| Analysis: $C_{14}H_{12}F_3N_3S_2$; molecular weight = 343.40 | | | | | |
|---|---|---|---|---|---|
| | % C | % H | % F | % N | % S |
| Calculated: | 48.97 | 3.52 | 16.60 | 12.24 | 18.67 |
| Found: | 49.0 | 3.4 | 16.6 | 12.2 | 18.6 |

| IR Spectrum (CHCl₃): | |
|---|---|
| CN | 2230 cm⁻¹ |
| aromatics + conjugated system | 1612, 1582, 1508 cm⁻¹ |
| CF₃ | 1178 cm⁻¹ |

EXAMPLE 14

4-(4,4-dimethyl-5-imino-2-thioxo-1-imidazolidinyl)-2-trifluoromethyl-benzonitrile 1 g of 2-amino-2-cyano-propane and 1 ml of tetrahydrofuran were added with stirring to a mixture of 2.54 g of the isocyanate product of Example 11, 20 ml of tetrahydrofuran and 0.2 ml of triethylamine at room temperature and was then evaporated to dryness. The 3.5 g of residue were chromatographed on silica and eluted with a 7-3 ethyl acetate-cyclohexane mixture and then a 1—1 ethyl acetate-cyclohexane mixture to obtain 940 mg of the desired product. 300 g were crystallized from isopropanol to obtain 263 mg of product melting at 296° C.

| Analysis: $C_{13}H_{11}F_3N_4S$; molecular weight = 312.32 | | | | | |
|---|---|---|---|---|---|
| | % C | % H | % F | % N | % S |
| Calculated: | 50.00 | 3.55 | 18.25 | 17.94 | 10.27 |

| Analysis: $C_{13}H_{11}F_3N_4S$; molecular weight = 312.32 | | | | | |
|---|---|---|---|---|---|
| | % C | % H | % F | % N | % S |
| Found: | 49.9 | 3.4 | 18.3 | 17.6 | 10.4 |

| IR Spectrum (Nujol): | |
|---|---|
| OH/NH | 3260 cm⁻¹ |
| CN | 2230 cm⁻¹ |
| C=S | 1764 cm⁻¹ |
| aromatic + C=C | 1612, 1575, 1530, 1501 cm⁻¹ |

A new preparation was effected using 1,2-dichloroethane in place of tetrahydrofuran to obtain the product in a 60% yield.

EXAMPLE 15

4-(4,4-dimethyl-5-oxo-3-thioxo-1-imidazolidinyl)-1-trifluoromethyl-benzonitrile A mixture of 635 mg of the product of Example 14 and 14 ml of 0.5 N hydrochloric acid was stirred for one hour at reflux and after cooling, 100 ml of water were added. The mixture was extracted with ethyl acetate and the organic phase was washed with aqueous sodium chloride, dried and evaporated to dryness. The 600 mg of residue were chromatographed and eluted with a 95-5 methylene chloride-acetone mixture to obtain 590 mg of product melting at 190° C. to 191° C. The latter was crystallized from isopropanol to obtain 490 mg of product melting to 190° C. to 191° C.

| Analysis: $C_{13}H_{10}F_3N_3OS$; molecular weight = 313.30 | | | | | |
|---|---|---|---|---|---|
| | % C | % H | % F | % N | % S |
| Calculated: | 49.84 | 3.22 | 18.19 | 13.41 | 10.23 |
| Found: | 49.6 | 3.1 | 18.4 | 13.2 | 10.0 |

| IR Spectrum (CHCl₃): | |
|---|---|
| =C—NH | 3430 cm⁻¹ |
| CN | 2230 cm⁻¹ |
| C=O | 1766 cm⁻¹ |
| aromatics and conjugated system | 1612, 1578, 1505 cm⁻¹ |

EXAMPLE 16

5,5-dimethyl-3-(4-nitro-3-trifluoromethyl-phenyl)-1-pentyl-2,4-imidazolidine Using the procedure of Example 1, 1 g of 1-(3-trifluoromethyl-4-nitro-phenyl)-4,4-dimethyl imidazolidien-2,5-dione was reacted with 170 mg of sodium hydride and 0.47 ml of 1-bromo-pentane to obtain after chromatography on silica and elution with an 8-2 methylene chloride-cyclohexane mixture 1.23 g of product which as crystallized from isopropanol to obtain 995 mg of the desired product melting at 84° C.

| Analysis: $C_{17}H_{20}O_4F_3N_3$; molecular weight = 387.35 | | | | |
|---|---|---|---|---|
| | % C | % H | % F | % N |
| Calculated: | 52.71 | 5.20 | 14.71 | 10.85 |
| Found: | 52.8 | 5.1 | 14.8 | 10.7 |

| IR Spectrum (CHCl₃): | |
|---|---|
| C=O | 1778, 1723 cm⁻¹ |
| NO₂ | 1544, 1360 cm⁻¹ |

EXAMPLE 17

5,5-dimethyl-3-(4-nitro-3-trifluoromethyl-phenyl)-1-nonyl-2,4-imidazolidinedione Using the procedure of Example 1, 1 g of 1-(3-trifluoromethyl-4-nitro-phenyl)-4,4-dimethyl imidazolidine-2,5-dione was reacted with a 50% suspension of 170 mg of sodium hydride in oil and 0.7 ml of 1-bromononane to obtain after chromatography on silica 1.08 g of the desired product melting at 63° C.

| Analysis: $C_{21}H_{28}O_4F_3N_3$; molecular weight = 443.46 | | | | |
|---|---|---|---|---|
| | % C | % H | % F | % N |
| Calculated: | 56.87 | 6.36 | 12.85 | 9.48 |
| Found: | 57.0 | 6.5 | 12.8 | 9.5 |

| IR Spectrum (CHCl₃): | |
|---|---|
| C=O | 1788, 1723 cm⁻¹ |
| NO₂ | 1544, 1359 cm⁻¹ |
| C=O | 1778, 1723 cm⁻¹ |
| NO₂ | 1544, 1360 cm⁻¹ |

EXAMPLE 17

5,5-dimethyl-3-(4-nitro-3-trifluoromethyl-phenyl)-1-nonyl-2,4-imidazolidinedione Using the procedure of Example 1, 1 g of 1-(3-trifluoromethyl-4-nitro-phenyl)-4,4-dimethyl imidazolidine-2,5-dione prepared from a 50% suspension of 170 mg of sodium hydride in oil and 0.7 ml of 1-bromononane were reacted to obtain after chromatography on silica 1.08 g of the desired product melting at 63° C.

| Analysis: $C_{21}H_{28}O_4F_3N_3$; molecular weight = 443.46 | | | | |
|---|---|---|---|---|
| | % C | % H | % F | % N |
| Calculated: | 56.87 | 6.36 | 12.85 | 9.48 |
| Found: | 57.0 | 6.5 | 12.8 | 9.5 |

| IR Spectrum (CHCl₃): | |
|---|---|
| C=O | 1788, 1723 cm⁻¹ |
| NO₂ | 1544, 1359 cm⁻¹ |

EXAMPLE 18

4-(3,4,4-trimethyl-2,5-dioxo-1-imidazolidinyl)-2-trifluoromethyl-benzonitrile

Using the procedure of Example 1, 300 mg of the product of Example 8 were reacted to obtain 275 mg of the desired product melting at 158° C.

| IR Spectrum (CHCl₃): | |
|---|---|
| C=O | 1780, 1727 cm⁻¹ |
| aromatics | 1615, 1574, 1505 cm⁻¹ |

| IR Spectrum (CHCl₃): | |
|---|---|
| CN | 2238 cm⁻¹ |

EXAMPLE 19

4-(5-thioxo-2-oxo-3,4,4-trimethyl-1-imidazolidinyl)-2-trifluoromethyl-benzonitrile (product A),
4-(5-oxo-2-thioxo-3,4,4-trimethyl-1-imidazolidinyl)-2-trifluoromethyl benzonitrile (product B) and
4-(2,5-dithioxo-3,4,4-trimethyl-1-imidazolidinyl)-2-trifluoromethyl-benzonitrile (product C)

A suspension of 230 mg of the product of Example 18, 1.4 ml of toluene and 78 mg of Lawesson reagent was refluxed for 9 hours and then returned to room temperature and evaporated to dryness. The 330 mg of residue was chromatographed on silica and eluted with a 99-1 methylenechloride-acetone mixture to obtain in the following order of elution 46 mg of product C with a melting point of 210° C. to 211° C. and a Rf=0.63 (identical to the product of Example 13), 26 mg of product B with a melting point of 170° C. to 171° C. and a Rf=0.49 (identical to the product of Example 12) and 42 mg of product A with a melting point of 194° C. and a Rf=0.34.

| Analysis for Product A | |
|---|---|
| IR Spectrum (CHCl₃): | |
| C=O | 1760 cm⁻¹ |
| CN | 2235 cm⁻¹ |
| aromatics | 1615, 1580, 1508 cm⁻¹ |

| UV Spectrum (ethanol): | | |
|---|---|---|
| max | 228 nm | $\epsilon$ = 19,400 |
| | 256 nm | $\epsilon$ = 12,100 |
| | 298 nm | $\epsilon$ = 8,600 |
| | 390 nm | $\epsilon$ = 70 |

EXAMPLE 20

4-(4,5-dihydro-4,4-dimethyl-2-methylthio-5-oxo-1H-imidazolidin-1-yl)-2-trifluoromethyl benzonitrile A solution of 626 mg of the product of Example 15 in 6 ml of dimethylformamide was added to a 50% suspension of 108 mg of sodium hydride in oil and 1.8 ml of dimethylformamide and after rinsing with 0.3 ml of dimethylformamide, the mixture was stirred for 10 minutes after cessation of hydrogen evolution. A mixture of 0.19 ml of methyliodide in 1 ml of dimethylformamide was added dropwise and after 45 minutes of reaction, the mixture was poured into 50 g of an ice-water mixture containing 0.5 g of monosodium phosphate. The mixture was extracted 4 times with ether and the combined organic phases were washed with aqueous sodium chloride, dried over magnesium sulfate and evaporated to dryness. The 668 mg of residue were chromatographed on silica and eluted with a 95-5 dichloromethane-ethyl acetate mixture to obtain 640mg of the desired product which chromatographed again on silica. Elution with a 7-3 cyclohexane-ethyl acetate mixture yielded after taking up in ether 507mg of the desired product melting at 62° C.

| IR Spectrum: | |
|---|---|
| C=O | 1747 cm$^{-1}$ |
| C=N and aromatics | 1614, 1581, 1563, 1503 cm$^{-1}$ |

| UV Spectrum (ethanol): | | |
|---|---|---|
| max | 209 nm | $\epsilon = 26,000$ |
| inflex. | 236 nm | $\epsilon = 11,500$ |
| inflex. | 264 nm | $\epsilon = 8,700$ |

EXAMPLE 21

4-(4,5-dihydro-4,4-dimethyl-5-oxo-2-benzylthio)-1H-imidazol-1-yl) 2-trifluoromethyl-benzonitrile A solution of 313 mg of 4-(4,4-dimethyl-5-oxo-2-thioxo-1-imidazolidinyl) 2-trifluoromethyl-benzonitrile in 3 ml of dimethylformamide were added to a suspension of 53 mg of sodium hydride in oil and 0.5 ml of dimethylformamide and after stirring for 10 minutes, 0.1 ml of benzyl bromide were added. The mixture was stirred for 30 minutes and then poured into an ice-water mixture containing 500 mg of monosodium phosphate. The mixture was extracted with ether and the organic phase was washed with aqueous sodium chloride, dried and evaporated to dryness. The 450 mg of residue were chromatographed on silica and eluted with a 97.5-2.5 methylene chloride-ethyl acetate mixture to obtain 316mg of the desired product with a RF=0.38.

| | Analysis: | | | |
|---|---|---|---|---|
| | %C | %H | %F | %N |
| Calculated: | 59.54 | 4.0 | 14.12 | 10.41 |
| Found: | 59.6 | 4.0 | 14.1 | 10.2 |

| IR Spectrum (CHCl$_3$): | |
|---|---|
| C=O | 1746 cm$^{-1}$ |
| CN | 2236 cm$^{-1}$ |
| aromatics and conjugated system | 1614, 1580, 1570, 1503, 1499 cm$^{-1}$ |

EXAMPLE 22

4-(4,4-dimethyl-3-(2-hydroxyethyl)-5-imino-2-thioxo-1-imidazolidinyl) 2-trifluoromethyl-benzonitrile 8 ml of ethanoline were added dropwise at 20° C. to 30° C. to 12.3 ml of the cyanhydrin of acetone and after stirring for 18 hours, the mixture was distilled to obtain 2.3 g of a mixture of 2-(2-hydroxyethyl)-amino-2-methyl-propanenitrile and 2,2-dimethyloxazolidine which was used as is for the next step.

A mixture of 1.18 g of the said mixture, 2.11 g of the isothiocyanate of Example 11 and 20 ml of tetrahydrofuran and 0.5 ml of triethylamine was refluxed for 30 minutes and then evaporated to dryness. The residue was chromatographed on silica and eluted with a 95–5 methylene chloride-acetone mixture to obtain 1.26 g of the desired product and 686 mg of N-(4-cyano-2-trifluoromethyl-phenyl)-2,2-dimethyl-3-oxazolidine carbothioamide. The 686 mg were dissolved in 10 ml of ethyl acetate and after the addition of 30 ml of cyclohexane, the mixture was concentrated to 4 ml and vacuum filtered and dried to obtain another 518 mg of product. The raw product was dissolved in 20 ml of isopropanol and the solution was concentrated to 5 ml, vacuum filtered and dried to obtain 1.04 g of the desired product melting at 181° C.

| | Analysis: | | | | |
|---|---|---|---|---|---|
| | %C | %H | %F | %N | %S |
| Calculated: | 50.55 | 4.24 | 16.00 | 15.72 | 9.00 |
| Found: | 50.4 | 4.1 | 15.9 | 15.6 | 9.0 |

| IR Spectrum (CHCl$_3$): | |
|---|---|
| OH | 3630 cm$^{-1}$ |
| =NH | 3314, 1677 cm$^{-1}$ |
| CN | 2230 cm$^{-1}$ |
| aromatics | 1611, 1576, 1504 cm$^{-1}$ |

EXAMPLE 23

4-(4,4-dimethyl-3-(2-hydroxyethyl)-5-oxo-2-thioxo-1-imidazolidinyl) 2-trifluoromethyl-benzonitrile (Product A) and 4-(4,4-dimethyl-2,5-dioxo-3-(2-mercaptoethyl) 1-imidazolidinyl)-2-trifluoromethyl-benzonitrile (Product B)

A mixture of 680 mg of the product of Example 22, 7 ml of water and 7 ml of hydrochloric acid was refluxed for 10 minutes and after cooling to room temperature, the mixture was extracted with ethyl acetate. The organic phase was washed with aqueous sodium chloride, dried and evaporated to dryness. The residue was chromatographed on silica and eluted with a 1—1 cyclohexane-ethyl acetate mixture to obtain 119 mg of product B with a Rf=0.35 and 569 mg of product A with a Rf=0.14 and a melting point of $\approx$130° C.

| Analysis: C$_{15}$H$_{14}$F$_3$N$_3$O$_2$S; molecular weight = 357.36 | | | | | |
|---|---|---|---|---|---|
| | %C | %H | %F | %N | %S |
| Calculated: Product A | 50.42 | 3.95 | 15.95 | 11.76 | 8.97 |
| Found: Product B | 50.7 | 4.0 | 15.7 | 11.5 | 9.1 |
| Found: | 50.6 | 3.8 | 15.9 | 11.6 | 9.1 |

| IR Spectrum (CHCl$_3$): | |
|---|---|
| Product A: | |
| OH | 3626 cm$^{-1}$ |
| CN | 2236 cm$^{-1}$ |
| C=O | 1763 cm$^{-1}$ |
| aromatics | 1615, 1578, 1504 cm$^{-1}$ |
| Product B: | |
| Absence of OH | |
| CN | 2228 cm$^{-1}$ |
| C=O | 1780, 1726 cm$^{-1}$ |
| aromatics | 1615, 1578, 1505 cm$^{-1}$ |

Using 4-(4,4-dimethyl-2,5-dioxo-1-imidazolidinyl)-2-trifluoromethyl-benzonitrile of Example 8 and the appropriate reactants, the following products were prepared.

EXAMPLE 24

4-(4,4-dimethyl-2,5-dioxo-3-ethyl-1-imidazolidinyl)-2-trifluoromethyl-benzonitrile with a melting point of 100° C. to 101° C.

| Analysis: $C_{15}H_{14}F_3N_3O_2$; molecular weight = 325.29 | | | | |
|---|---|---|---|---|
| | %C | %H | %F | %N |
| Calculated: | 55.39 | 4.34 | 17.52 | 12.92 |
| Found: | 55.7 | 4.3 | 17.6 | 12.8 |

| IR Spectrum (CHCl₃): | |
|---|---|
| CN | 2238 cm⁻¹ |
| C=O | 1777, 1724 cm⁻¹ |
| aromatics | 1617, 1575, 1505 cm⁻¹ |

EXAMPLE 25

4-(4,4-dimethyl-2,5-dioxo-3-(2-propenyl)-1-imidazolidinyl)-2-trifluoromethyl-benzonitrile melting at 109° C. to 110° C.

| Analysis: $C_{16}H_{14}F_3N_3O_2$; molecular weight = 337.35 | | | | |
|---|---|---|---|---|
| | %C | %H | %F | %N |
| Calculated: | 56.97 | 4.18 | 16.90 | 12.46 |
| Found: | 57.0 | 4.1 | 16.2 | 12.3 |

| IR Spectrum (CHCl₃): | |
|---|---|
| CN | 2238 cm⁻¹ |
| C=O | 1728, 1725 cm⁻¹ |
| HC=CH₂ | 1645 cm⁻¹ |
| aromatics | 1616, 1575, 1505 cm⁻¹ |

EXAMPLE 26

4-(4,4-dimethyl-2,5-dioxo-3-benzyl-1-imidazolidinyl)-2-trifluoromethyl-benzonitrile melting at 98° C. to 99° C.

| Analysis: $C_{20}H_{16}F_3N_3O_2$; molecular weight = 387.36 | | | | |
|---|---|---|---|---|
| | %C | %H | %F | %N |
| Calculated: | 62.01 | 4.16 | 14.71 | 10.85 |
| Found: | 62.0 | 4.1 | 14.7 | 10.8 |

| IR Spectrum (CHCl₃): C—NH: 3430 cm⁻¹ | |
|---|---|
| CN | 2238 cm⁻¹ |
| C=O | 1779, 1724 cm⁻¹ |
| aromatics | 1615, 1605, 1575, 1504, 1497 cm⁻¹ |

EXAMPLE 27

4-(4,4-dimethyl-2,5-dioxo-3-(4-fluorobenzyl)-1-imidazolidinyl-2-trifluoromethyl-benzonitrile melting at 101°° C. to 102° C.

| Analysis: $C_{20}H_{15}F_4N_3O_2$; molecular weight = 405.35 | | | | |
|---|---|---|---|---|
| | %C | %H | %F | %N |
| Calculated: | 59.26 | 3.73 | 18.75 | 10.37 |
| Found: | 59.1 | 3.5 | 18.9 | 10.3 |

| IR Spectrum (CHCl₃): | |
|---|---|
| CN | 2238 cm⁻¹ |
| C=O | 1780, 1724 cm⁻¹ |
| aromatics | 1615, 1612, 1505 cm⁻¹ |

EXAMPLE 28

4-(4,4-dimethyl-2,5-dioxo-3-(4-methoxybenzyl)-1-imidazolidinyl-benzonitrile melting at 95° C. to 96° C.

| Analysis: $C_{21}H_{18}F_3N_3O_3$; molecular weight = 417.39 | | | | |
|---|---|---|---|---|
| | %C | %H | %F | %N |
| Calculated: | 60.43 | 4.35 | 13.65 | 10.07 |
| Found: | 59.1 | 3.5 | 18.9 | 10.3 |

| IR Spectrum (CHCl₃): | |
|---|---|
| CN | 2238 cm⁻¹ |
| C=O | 1778, 1723 cm⁻¹ |
| aromatics | 1615, 1584, 1514, 1505 cm⁻¹ |

EXAMPLE 29

4-(4,4-dimethyl-2,5-dioxo-3-(4-trifluoromethyl-benzyl)-1-imidazolidinyl)-2-trifluoromethyl benzonitrile melting at ≈89° C. to 90° C.

| Analysis: $C_{21}H_{15}F_6N_3O_2$; molecular weight = 313.30 | | | | |
|---|---|---|---|---|
| | %C | %H | %F | %N |
| Calculated: | 55.39 | 3.32 | 25.03 | 9.23 |
| Found: | 55.2 | 3.2 | 25.3 | 9.2 |

| IR Spectrum (CHCl₃): | |
|---|---|
| CN | 2238 cm⁻¹ |
| C=O | 1615, 1505 cm⁻¹ |
| aromatics | 1615, 1505 cm⁻¹ |

EXAMPLE 30

4-(4,4-dimethyl-2,5-dioxo-3-(2-epoxymethyl)-1-imidazolidinyl 2-trifluoromethyl-benzonitrile melting at 112° C. to 113° C.

| Analysis: $C_{16}H_{14}F_3N_3O_3$; molecular weight = 353.30 | | | | |
|---|---|---|---|---|
| | %C | %H | %F | %N |
| Calculated: | 54.39 | 3.99 | 16.13 | 11.89 |
| Found: | 54.7 | 4.0 | 16.1 | 11.8 |

| IR Spectrum (CHCl₃): | |
|---|---|
| CN | 2235 cm⁻¹ |
| C=O | 1781, 1725 cm⁻¹ |
| aromatics | 1615, 1576, 1505 cm⁻¹ |

EXAMPLE 31

4-(4,4-dimethyl-2,5-dioxo-3-propyl-1H-imidazolidinyl)-2-trifluoromethyl benzonitrile melting at 113° C. to 114° C.

| Analysis: $C_{16}H_{16}F_3N_3O_2$; molecular weight = 339.32 | | | | |
|---|---|---|---|---|
| | %C | %H | %F | %N |
| Calculated: | 56.64 | 4.75 | 16.80 | 12.38 |
| Found: | 56.7 | 4.7 | 16.7 | 12.2 |

| IR Spectrum (CHCl$_3$): | |
|---|---|
| CN | 2236 cm$^{-1}$ |
| C=O | 1778, 1725 cm$^{-1}$ |
| aromatics | 1616, 1505 cm$^{-1}$ |

EXAMPLE 32

4-(4,4-dimethyl-2,5-dioxo-3-isopropyl-1-imidazolidinyl)-2-trifluoromethyl benzonitrile melting at 138° C. to 139° C.

| Analysis: $C_{16}H_{16}F_3N_3O_2$; molecular weight = 339.32 | | | | |
|---|---|---|---|---|
| | %C | %H | %F | %N |
| Calculated: | 56.64 | 4.75 | 16.80 | 12.38 |
| Found: | 56.5 | 4.7 | 17.1 | 12.3 |

| IR Spectrum (CHCl$_3$): | |
|---|---|
| CN | 2236 cm$^{-1}$ |
| C=O | 1778, 1724 cm$^{-1}$ |
| aromatics | 1616, 1575, 1505 cm$^{-1}$ |

Using 4-(4,4-dimethyl-5-oxo-2-thioxo-1-imidazolidinyl)-2-trifluoromethyl benzonitrile of Example 15 and the appropriate reactants, the following compounds were prepared:

EXAMPLE 33

4-(4,5-dihydro-4,4-dimethyl-2-nonylthio-5-oxo-1H-imidazol-1-yl) 2-trifluoromethyl-benzonitrile were a Rf=0.35 (97.5-2.5 methylene chloride-ethyl acetate eluant).

EXAMPLE 34

4-(4,5-dihydro-4,5-dimethyl-2-(3-hydroxypropylthio)-5-oxo-1H-imidazol-1-yl) 2-trifluoromethyl-benzonitrile with a Rf=0.17 (8-2 methylene chloride-ethyl acetate eluant).

EXAMPLE 35

Ethyl [1-(4-cyano-3-trifluoromethyl-phenyl)-4,5-dihydro-4,4-dimethyl-5-oxo-1H-imidazol 2-yl)-thio]-acetate with a Rf=0.20 (65–35 cyclohexane-ethyl acetate eluant).

Using the isocyanate of Example 11 and the appropriate reactants, the following compounds were prepared.

EXAMPLE 36

4-(4,4-dimethyl-3-ethyl-5-imino-2-thioxo-1-imidazolidinyl)-2-trifluoromethyl benzonitrile with a Rf=0.16 (95-5 methylene chloride-acetone eluant).

EXAMPLE 37

4-(4,4-dimethyl-5-imino-3-pentyl-2-thioxo-1-imidazolidinyl)-2-trifluoromethyl benzonitrile with a RF=0.35 (8-2 ethyl acetate-cyclohexane eluant)

Using the 4-(4,4-dimethyl-3-ethyl-5-imino-2-thioxo-1-imidazolidinyl)-2-trifluoromethyl benzonitrile of Example 36 and the 4-(4,4-dimethyl-5-imino-3-pentyl-2-thioxo-1-imidazolidinyl) 2-trifluoromethyl-benzonitrile of Example 37 and 0.5 N hydrochloric acid, the following compounds were prepared.

EXAMPLE 38

4-(4,4-dimethyl-3-ethyl-5-oxo-2-thioxo-1-imidazolidinyl)-2-trifluoromethyl benzonitrile with a Rf=0.38 (1—1 ethyl acetate-cyclohexane eluant).

EXAMPLE 39

4-(4,4-dimethyl-5-oxo-3-pentyl-2-thioxo-1-imidazolidinyl)-2-trifluoromethyl benzonitrile with a melting point of 78° C. and a Rf=0.66 (8-2 ethyl acetate-cyclohexane eluant)

Using 4-(4,5-dihydro-4,4-dimethyl-2-methylthio-5-oxo-1H-imidazol-1-yl) 2-trifluoromethyl-benzonitrile of Example 20 and 4-(4,5-dihydro-4,4-dimethyl-5-oxo-2-benzylthio-1H-imidazol-1-yl) 2-trifluoromethyl-benzonitrile of Example 21 and the Lawesson reagent, the following compounds were prepared.

EXAMPLE 40

4-(4,5-dihydro-4,4-dimethyl-2-methylthio-5-thioxo-1H-imidazol-1-yl) 2-trifluoromethyl-benzonitrile with a Rf=0.36 (97.5-2.5 methylene chloride-ethyl acetate eluant).

EXAMPLE 41

4-(4,5-dihydro-4,4-dimethyl-2-benzylthio-5-thioxo-1H-imidazol-1-yl) 2-trifluoromethyl-benzonitrile with a Rf=0.62 (98-2 methylene chloride-ethyl acetate eluant).

EXAMPLE 42

3-(4-cyano-3-trifluoromethyl-penyl)-5,5-dimethyl-2,4-dioxo-N-methyl-N-isopropyl-1-imidazolidine acetamide 0.1 ml of N-methyl-morpholine was added to a suspension of 3-(4-cyano-3-trifluoromethyl-phenyl)-5,5-dimethyl-2,4-dioxo-1-acetic acid in 4 ml of methylene chloride and after cooling the solution to −10° C., 0.1 ml of isobutyl chloroformate was added dropwise. After stirring for 25 minutes at −10° C., 0.15 ml of N-methyl-N-isopropylamine was added and the mixture was allowed to return to room temperature over 40 minutes. 5 ml of an aqueous saturated sodium bicarbonate solution were added and after stirring for 30 minutes, the mixture was extracted with methylene chloride. The organic phase was washed with water, dried and evaporated to dryness under reduced pressure. The residue was chromatographed on silica and eluted with a 96-4 methylene chloride-acetone mixture to obtain 147 mg of the desired product.

| IR Spectrum (CHCl$_3$): | |
|---|---|
| CN | 2236 cm$^{-1}$ |
| hydantoin C=O | 1783, 1728 cm$^{-1}$ |
| amide C=O | 1661 cm$^{-1}$ |

EXAMPLE 43

4-(4,4-dimethyl-2,5-dioxo-3-(2-hydroxyethyl)-1-imidazolidinyl) 2-trifluoromethyl-benzonitrile Using the procedure of Example 9, 900 mg of the product of Example 8 and 1.91 g of 2-bromoethane tert.-butyldimethylsilyl ether were reacted to obtain 1 g of the silyloxy ether derivative melting at 86° C. to 87° C. after chromatography on silica and elution with a 7 g cyclohexane-ethyl acetate mixture.

1 ml of 2 N hydrochloric acid were added to a mixture of 380 mg of the silyloxy ether, 4 ml of methanol and 1 ml of methylene chloride and after stirring for 40 minutes at room temperature,the mixture was poured into 15 ml of water and was extracted with methylene chloride. The organic phase was washed with water, dried and evaporated to dryness and the residue was chromatographed on silica. Elution with a 7-3 methylene chloride-ethyl acetate mixture yielded the desired product which after crystallization from isopropanol melted at 109° C. to 110° C. and had a Rf=0.9.

|  | Analysis: | | | |
| --- | --- | --- | --- | --- |
|  | %C | %H | %F | %N |
| Calculated: | 52.79 | 4.23 | 16.70 | 12.31 |
| Found: | 52.5 | 4.2 | 16.7 | 12.1 |

EXAMPLE 44

Using the procedure of Example 43, 2-bromopropanol tert.-butyldimethylsilyl ether was reacted to obtain 4-(4,4-dimethyl-2,5-dioxo-3-(3-hydroxypropyl) 1-imidazolidinyl)-2-trifluoromethyl-benzonitrile melting at 131° C. to 132° C. and a Rf=0.13 (3-1 methylene chloride-ethyl acetate eluant).

EXAMPLE 45

4-[3-(2-acetyloxyethyl)-4,4-dimethyl-2,5-dioxo-1-imidazolidinyl]2-trifluoromethyl-benzonitrile A mixture of 215 mg of the product of Example 43, 15 mg of 4-dimethylamino-pyridine, 1 ml of pyridine and 0.5 ml of acetic acid anhydride was stirred at room temperature for 30 minutes and was then poured into 20 ml of a saturated aqueous sodium bicarbonate solution. After stirring for 20 minutes, the mixture was extracted with ethyl acetate. The organic phase was washed with water and evaporated to dryness and the pyridine and residual acetic acid were distilled. The residue was chromatographed on silica and eluted with a 65-35 methylene chloride-ethyl acetate mixture. The residue with a Rf=0.35 was taken up in isopropanol, partially concentrated, iced and vacuum filtered to obtain after drying 210 mg of the desired product melting at 99° C. to 100° C.

|  | Analysis: | | | |
| --- | --- | --- | --- | --- |
|  | %C | %H | %F | %N |
| Calculated: | 53.27 | 4.21 | 14.87 | 10.96 |
| Found: | 53.5 | 4.3 | 15.2 | 10.9 |

Using the above procedure, the following products were prepared.

EXAMPLE 46

4-(4,4-dimethyl-2,5-dioxo-3-(5-hydroxypentyl)-1-imidazolidinyl) 2-trifluoromethyl-benzonitrile melting at 101° C. to 102° C.

EXAMPLE 47

4-(4,4-dimethyl-2,5-dioxo-3-(2-methoxyethyl)-1-imidazolidinyl) 2-trifluoromethyl-benzonitrile melting at 68° C. to 69° C.

EXAMPLE 48

4-(4,4-dimethyl-2,5-dioxo-3-cyanomethyl-1-imidazolidinyl)-2-trifluoromethyl benzonitrile melting at 186° C. to 187° C.

EXAMPLE 49

4-(4,4-dimethyl-2,5-dioxo-3-[(1,3-dioxolan-2-yl)-methyl]-1-imidazolidinyl) 2-trifluoromethyl-benzonitrile melting at 135° C. to 136° C.

EXAMPLE 50

4-(4,4-dimethyl-2,5-dioxo-3-(2-chloroethyl)-1-imidazolidinyl) 2-trifluoromethyl-benzonitrile melting at 120° C. to 121° C.

EXAMPLE 51

1-(3,4-dichlorophenyl)-5-imino-3,4,4-trimethyl-2-imidazolidine thione

A mixture of 2.4 g of the isocyanate of 3,4-dichlorophenyl, 1.3 ml of 2-methylamino-2-cyano-propane, 23 ml of tetrahydrofuran and 0.23 ml of triethylamine was refluxed for 16 hours and then evaporated to dryness under reduced pressure. The residue was chromatographed on silica and eluted with a 96-4 methylene chloride-acetone mixture to obtain after crystallization from ether, 2.54 g of the desired product melting at 133° C.

EXAMPLE 52

3-(3,4-dichlorophenyl)-2-thioxo-1,5,5-trimethyl-1-imidazolidinone

A suspension of 1.88 g of the product of Example 51 in 14 ml of 6 N hydrochloric acid was refluxed for 45 minutes and after the addition of another 14 ml of 6 N hydrochloric acid, the mixture was refluxed for 2 more hours. Another 4 ml of 6 N hydrochloric acid were added and the mixture was refluxed for 90 minutes and then returned to room temperature. 100 g of ice were added and the mixture was extracted with ethyl acetate. The organic phase was washed with water, dried and evaporated to dryness. The residue was chromatographed on silica and eluted with a 1—1 cyclohexane-ethyl acetate mixture to obtain 1.84 g of the desired product melting at 129° C. after crystallization from isopropanol.

| Analysis: $C_{12}H_{12}Cl_2N_2OS$; molecular weight = 303.21 | | | | | |
| --- | --- | --- | --- | --- | --- |
|  | %C | %H | %Cl | %N | %S |
| Calculated: | 47.54 | 3.99 | 23.38 | 9.24 | 10.57 |
| Found: | 47.5 | 3.8 | 23.2 | 9.3 | 10.5 |

| IR Spectrum (CHCl$_3$): | |
|---|---|
| C=O | 1753 cm$^{-1}$ |
| C=S + aromatics | 1595, 1570, 1496 cm$^{-1}$ |

Using the above procedures, the following compounds were prepared:

EXAMPLE 53

3-(3,4-dichlorophenyl)-3,5-dihydro-5,5-dimethyl-2-methylthio-4H-imidazol 4-one melting at 110° C.

EXAMPLE 54

1-(3,4-dichlorophenyl)-3,4-4-trimethyl-2,5-imidazolidine-dithione melting at ≈146° C.

EXAMPLE 55

1-(4-chloro-3-trifluoromethyl-phenyl)-4,4-dimethyl-2-thioxo-5-imidazolidinone melting at 176° C.

EXAMPLE 56

1-(4-chloro-3-trifluoromethyl-phenyl)-4,4-dimethyl-5-imino-2-imidazolidinethione melting at 173° C. to 174° C.

EXAMPLE 57

3-(3,4-dichlorophenyl)-3,5-dihydro-5,5-dimethyl-2-benzylthio 4H-imidazol-4-one

| IR Spectrum (CHCl$_3$): | |
|---|---|
| C=O | 1736 cm$^{-1}$ |
| CN + aromatics | 1578, 1496 cm$^{-1}$ |

EXAMPLE 58

4-(4,4-dimethyl 2,5-dioxo 3-(4-hydroxy butyl) 1-imidazolidinyl) 2-(trifluoromethyl) benzonitrile a) Condensation 600 mg of 4-(4,4-dimethyl-2,5-dioxo-1-imidazolidinyl)-2-(trifluoromethyl) benzonitrile obtained as in Example 8—in 5 ml of dimethylformamide were added to a suspension of 104 mg of sodium hydride in 0.8 ml of dimethylformamide, while maintaining the temperature below 20° C. After 10 minutes of stirring, 445 mg of 4-chloro-t-butyl-dimethylsilylether and 300 mg of sodium iodide were added. The mixture was heated for 16 hours at 50° C. and then, cooled to ambient temperature. 87 mg of sodium hydride were added followed by another 400 mg of the chlorinated ether and 267 mg of sodium hydride were added. The mixture was heated for another hour and then, returned to ambient temperature, and poured into 60 ml of water containing 600 mg of monopotassium phosphate. Extraction was carried out with ether and the organic phase was washed with water, dried and the solvent was evaporated. The residue was chromatographed on silica (eluant: methylene chloride—acetone (99-1)) to obtain 526 mg of product which as used as is for the stage following the cleavage.

The said product was mixed in 5 ml of methanol and 1.5 ml of 2 N hydrochloric acid and the mixture was stirred for 40 minutes at ambient temperature. The mixture was poured into 30 ml of water and was extracted with methylene chloride. The organic phase was washed with water, dried and the solvent was evaporated. After chromatographing the residue on silica (eluant methylene chloride—acetone (9-1), the fractions with a Rf=0.15, were recovered, and after crystallization from isopropyl ether, 307 mg of the expected product melting at 102°-103° C. were obtained.

| Analysis: C$_{17}$H$_{18}$F$_3$N$_3$O$_3$; molecular weight = 369.35 | | | | |
|---|---|---|---|---|
| | C% | H% | F% | N% |
| Calculated | 55.28 | 4.91 | 15.43 | 11.38 |
| Found | 55.2 | 4.9 | 15.3 | 11.1 |

| IR Spectrum (CHCl$_3$); | |
|---|---|
| OH | 3628 cm$^{-1}$ |
| C≡N | 2236 cm$^{-1}$ |
| C=O | 1778-1724 cm$^{-1}$ |
| Aromatics | 1615-1575-1505 cm$^{-1}$ |

Preparation of the 4-chloro t-buryl dimethylsilylether used at the start of Example 58.

9.9 ml of 4-chloro-1-butanol and 24.3 g of imidazole in 50 ml of tetrahydrofuran were stirred and 2.82 g of terbutyldimethylsilyl chloride in 20 ml of tetrahydrofuran were added dropwise at a temperature of less than 20° C. The mixture was stirred for 18 hours at ambient temperature, followed by separating, rinsing with tetrahydrofuran and eliminating the solvent under reduced pressure. The residue was purified by chromatography on silica (eluant: cyclohexane—ethyl acetate (95-5)) to obtain 17.5 g of the expected product.

EXAMPLE 59

(1,1-dimethyl) ethyl 3-(4-cyano 3-trifluoro-methyl-phenyl)5,5-dimethyl 2,4-dioxo-1-imidazolidine acetate 450 mg of the product of Example 8—in solution in 4 ml of dimethylformamide were added to a suspension of 78 mg of sodium hydride at 50% in oil and 0.5 ml of dimethylformamide. The mixture was stirred for 15 minutes and then without exceeding 30° C., 0.22 ml of terbutyl bromoacetate were slowly added. The mixture was stirred for 16 hours and then, was poured into 50 g of a water and ice mixture (1—1). 0.5 g of monopotassium phosphate were added and extraction was carried out with ether. The organic phase was washed with water, dried and evaporated to dryness. The 1.1 g of crude product was chromatographed on silica (eluant: methylene chloride—acetone (99-1)) to obtain 425 mg of the expected product melting at 122°-123° C. with a Rf=0.28 (eluant: methylene chloride—acetone (99-1))

| IR Spectrum (CHCl$_3$); | |
|---|---|
| C=O | 1788-1729 cm$^{-1}$ (hydantoin) 1745 cm$^{-1}$ (ester) |
| C≡N | 2235 cm$^{-1}$ |
| Aromatics | 1616-1505 cm$^{-1}$ |

| UV Spectrum (EtOH) |
|---|
| Max. 258 nm = 16100 |
| Infl. 277 nm = 6000 |
| Infl. 285 nm = 3000 |

EXAMPLE 60 cyclopentyl 3-(4-cyano-3-trifluoromethyl phenyl)-5,5-dimethyl 2,4-dioxo 1-imidazolidine acetate A solution of 355 mg of the product of Example 9,—49 mg of 4-dimethylamino-pyridine 130 mg of cyclopentanol and 6.5 ml of methylene chloride was cooled to −10° C. and then 226 mg of dicyclohexylcarbodiimide in 2 ml of methylene chloride were added. The mixture was allowed to return to ambient temperature, stirred for 25 minutes, heated at reflux for 2 hours, returned to ambient temperature, filtered and the solvent was evaporated. The residue was chromatographed on silica (eluant: methylene chloride—acetone (99-1)) to obtain 281 mg of the expected product with a Rf=0.25 (eluant: methylene chloride—acetone (99-1))

| IR Spectrum (CHCl$_3$); | |
|---|---|
| C=O | 1786-1729 cm$^{-1}$ (hydantoin) 1748 cm$^{-1}$ (ester) |
| C≡N | 2235 cm$^{-1}$ |
| Aromatics | 1615-1602-1576-1505 cm$^{-1}$ |

| UV Spectrum (EtOH) |
|---|
| Max. 258 nm = 16800 |
| Infl. 276 nm = 5800 |
| Infl. 286 nm = 3000 |

EXAMPLE 61 ethyl 3-(4-cyano 3-(trifluoromethyl) phenyl) 5,5-dimethyl 2,4-dioxo 1-imidazolidinebutanoate Using the procedure of Example 59, the product of Example 8—and ethyl 4-bromobutyrate were reacted to obtain the expected product melting at 66°-67° C. with a Rf=0.16 (eluant: methylene chloride—acetone (99-1))

| IR Spectrum (CHCl$_3$); | |
|---|---|
| C=O | 1770-1726 cm$^{-1}$ |
| C≡N | 2235 cm$^{-1}$ |
| Aromatics | 1616-1576-1505 cm$^{-1}$ |

| UV Spectrum (EtOH) |
|---|
| Max. 260 nm = 15500 |
| Infl. 277 nm = 7000 |
| Infl. 286 nm = 3600 |

EXAMPLE 62

3-(4-cyano 3-trifluoromethyl-phenyl) 5,5-dimethyl 2,4-dioxo 1-imidazolidine butanoic acid 1 g of the product of Example 61 in 20 ml of methanol was stirred for 3 hours at ambient temperature in the presence of 3 ml of 2 N sodium hydroxide and the mixture was poured into 20 ml of water and acidified to pH=1 using 7 ml of N hydrochloric acid. The mixture was extracted with ether and the extracts were washed with water and dried and the solvents were eliminated under reduced pressure to obtain 863 mg of crude product melting at 179°-180°C. which was purified by chromatography on silica (eluant: methylene chloride—methanol (92.5-7.5)). After crystallization from isopropanol, 614 mg of the expected product melting at 184°-185° C. and with a Rf=0.25 (eluant: methylene chloride—methanol (92.5-7.5)) were obtained.

| IR Spectrum (nujol); | |
|---|---|
| C=O | 1770-1753-1735-1712-1690-1645 cm$^{-1}$ |
| C≡N | 2230 cm$^{-1}$ |
| Aromatics | 1613-1587-1533-1502 cm$^{-1}$ |

EXAMPLE 63

(1,1-dimethyl) ethyl 3-(4-cyano 3-trifluoro-methyl-phenyl)-5,5-dimethyl 2,4-dioxo-1-imidazolidine-butanoate By carrying out the esterification of the product of Example 62, with terbutanol in the presence of dicyclohexylcarbodiimide and 4-dimethylamino-pyridine as in Example 60, the expected product melting at 96°-97° C. with a Rf=0.32 (eluant: methylene chloride—acetone (98-2)) was obtained.

| IR Spectrum (CHCl$_3$); | |
|---|---|
| C=O | 1779-1725 cm$^{-1}$ |
| C≡N | 2235 cm$^{-1}$ |
| Aromatics | 1616-1576-1505 cm$^{-1}$ |

| UV Spectrum (EtOH) |
|---|
| Max. 261 nm = 15600 |
| Infl. 276 nm = 7800 |
| Infl. 286 nm = 3700 |

EXAMPLE 64 cyclopentyl 3-(4-cyano 3-trifluoromethyl-phenyl) 5,5-dimethyl-2,4-dioxo-1-imidazolidine butanoate Using the procedure of Example 63, cyclopentanol was reacted to obtain the expected product melting at 85°-86° C. with a Rf=0.33 (eluant: methylene chloride-—acetone (98-2)).

| IR Spectrum (CHCl$_3$) | |
|---|---|
| C=O | 1779-1728 cm$^{-1}$ |
| C≡N | 2236 cm$^{-1}$ |
| Aromatics | 1616-1578-1505 cm$^{-1}$ |

| UV Spectrum (EtOH) |
|---|
| Max. 261 nm = 16000 |
| Infl. 277 nm = 7600 |
| Infl. 286 nm = 3700 |

EXAMPLE 65

4-(4,4-dimethyl-2,5-dioxo 3-(2-(4-fluorophenylthio) ethyl)-1-imidazolidinyl-2-(trifluoromethyl)-benzonitrile a) Formation of the phenolate 0.16 ml of 4-fluorothiophenol in 1.6 ml of dimethylformamide were added at a temperature of less than 28° C. to a suspension of 80 mg of sodium hydride in 0.5 ml of dimethylformamide, and the solution was stirred for 10 minutes.

b) Substitition 548 mg of 4-[4,4-dimethyl-2,5-dioxo-3-(2-chloroethyl) 1-imidazolidinyl]-2-(trifluoromethyl) benzonitrile (Example 50—in solution in 4 ml of dimethylformamide were added to the solution of a) and the mixture was stirred for 2 hours, poured into 50 ml of water with 0.5 g of monopotassium phosphate. Extraction was carried out with ether and the organic phase was washed with water and dried and the solvent was evaporated. After chromatographing the residue on silica (eluant: cyclohexane—ethyl acetate (75-25)), 570 mg of the expected product melting at 93°-94° C. with a Rf=0.29 (eluant: cyclohexane—ethyl acetate (75-25)) were obtained.

| IR Spectrum (CHCl₃) | |
|---|---|
| C=O | 1780-1726 cm⁻¹ |
| C≡N | 2238 cm⁻¹ |
| Aromatics | 1616-1579-1506 cm⁻¹ |
| (fluorophenyl) thio | 1591-1492 cm⁻¹ |

| UV Spectrum (EtOH) | |
|---|---|
| Max. 254 nm | = 18600 |
| Infl. 277 nm | = 7500 |
| Infl. 286 nm | = 4200 |

EXAMPLE 66

4-(4,4-dimethyl-2,5-dioxo-3-(2-(4-fluorophenyl sulfonyl) ethyl)-1-imidazolidinyl-2-(trifluoromethyl) benzonitrile 1.21 g of metachloroperbenzoic acid in 24 ml of methylene chloride were added dropwise at a temperature of less than 29° C. to 222 mg of the product of Example 65 in 4.4 ml of methylene chloride. After 30 minutes of stirring, the mixture was poured into 30 ml of sodium thiosulfate (0.5 M/1). The mixture was stirred for 10 minutes, followed by decanting and extracting with methylene chloride. The organic phase was washed with a saturated aqueous solution of sodium bicarbonate, then with water, dried, and the solvent was evaporated. After chromatographing the residue on silica (eluant: cyclohexane—ethyl acetate (1—1)), 220 mg of product were obtained which was crystallized from isopropanol to obtain 196 mg of the expected product melting at 155°-156° C. with a Rf=0.22 (eluant: ethyl acetate—cyclohexane (1—1)).

| IR Spectrum (CHCl₃); | |
|---|---|
| C=O | 1783-1727 cm⁻¹ |
| C≡N | 2236 cm⁻¹ |
| Aromatics | 1615-1593-1505-1497 cm⁻¹ |
| SO₂ | 1314-1150 cm⁻¹ |

| UV Spectrum (EtOH) | |
|---|---|
| Max. 258 nm | = 16700 |
| Infl. 286 nm | |

EXAMPLE 67

4-(4,4-dimethyl 2,5-dioxo 3-(2-((4-fluorophenyl) sulfinyl) ethyl) 1-imidazolidinyl 2-(trifluoromethyl) benzonitrile 222 mg of the product of Example 65 in 15 ml of methanol were stirred for 30 minutes at ambient temperature in the presence of 5 ml of an aqueous solution of sodium metaperiodate (0.1 M/1). The suspension was heated for one hour at 40° C. and 10 ml of methanol and 5 ml of oxidizing solution were added. The methanol was evaporated off and after 10 ml of a saturated solution of sodium chloride were added, extraction was carried out with ethyl acetate. The organic phase was washed with salt water, dried, and the solvent was evaporated. After chromatographing the residue on silica (eluant: methylene chloride—acetone (9-1)), 205 mg of product were obtained which was crystallized from isopropanol to obtain 180 mg of the expected product melting at 145°-146° C. with a Rf=0.10 (eluant: methylene chloride—acetone (9-1)).

| IR Spectrum (CHCl₃); | |
|---|---|
| C=O | 1782-1727 cm⁻¹ |
| C≡N | 2236 cm⁻¹ |
| Aromatics | 1615-1592-1505-1493 cm⁻¹ |

| UV Spectrum (EtOH) | |
|---|---|
| Max. 258 nm | ε = 17600 |
| Infl. 285 nm | |

Using the procedure of the preceding examples, 4-(4,4-dimethyl-2,5-dioxo-1-imidazolidinyl) 2-(trifluoromethyl) benzonitrile of Example 8—and the appropriate reagents, the compounds of the following examples were obtained:

EXAMPLE 68

4-(4,4-dimethyl 2,5-dioxo 3-((3-methoxyphenyl) methyl) 1-imidazolidinyl 2-(trifluoromethyl) benzonitrile Melting at 88°-89° C. with a Rf=0.21 (eluant: cyclohexane—ethyl acetate (7-3))

| IR Spectrum (CHCl₃) | |
|---|---|
| C=O | 1779-1724 cm⁻¹ |
| C≡N | 2238 cm⁻¹ |
| Aromatics | 1614-1602-1588-1575-1504-1491 |

| UV Spectrum (EtOH) | |
|---|---|
| Max. 260 nm | ε = 16800 |
| Infl. 210 nm | ε = 28500 |
| Infl. 280 nm | ε = 8900 |

EXAMPLE 69

4-(4,4-dimethyl 2,5-dioxo 3-(2-(4-morpholinyl) ethyl) 1-imidazolidinyl 2-(trifluoromethyl) benzonitrile with a Rf=0.20 (eluant: methylene chloride—acetone (70-30))

| IR Spectrum (CHCl₃) | |
|---|---|
| C=O | 1779-1725 cm$^{-1}$ |
| C≡N | 2235 cm$^{-1}$ |
| Aromatics | 1616-1576-1505 cm$^{-1}$ |
| morpholinyl | 1117 cm$^{-1}$ |

| UV Spectrum (EtOH) | |
|---|---|
| Max. 261 nm | ε = 14000 |
| Infl. 277 nm | ε = 6900 |
| Infl. 286 nm | ε = 3600 |

EXAMPLE 70

4-(4,4-dimethyl 3-(2-hydroxyethyl) 5-imino 2-thioxo 1-inidazolidinyl) 2-(trifluoromethyl)-benzonitrile a) Preparation of the isothiocyanate 2.23 g of 1-trifluoromethyl-4-amino benzonitrile (prepared accord to EP 0002892) were added slowly to a solution of 22 ml of distilled water and 1 ml of thiophosgene and the mixture was stirred for one hour and then extracted with chloroform. The extracts were washed with salt water, dried and evaporated to dryness under reduced pressure to obtain 3 g of product which was used as is for obtaining the imine.

b) Obtaining the imine 5 g of the said isothiocyanate were mixed with 37 ml of tetrahydrofuran in the presence of 1.5 ml of triethylamine and 2.8 g of 2-[(2-hydroxy ethyl) amino] 2-methyl propane nitrile (prepared in Example 22)—in solution in 10 ml of tetrahydrofuran were added all at once. The temperature spontaneously increased to 34° C. and the resultant mixture was allowed to return to ambient temperature while stirring for one hour. The solvent was evaporated off and the residue was chromatographed on silica (eluant: methylene chloride—methanol (7-3)) to obtain 5.87 g of the expected product melting at 181° C., after crystallization from isopropanol.

EXAMPLE 71

4-(4,4-dimethyl 3-(2-hydroxyethyl) 5-oxo 2-thioxo 1-imidazolidinyl) 2-(trifluoromethyl) benzonitrile 4.6 g of the product of Example 70 in 65 ml of methanol was refluxed for one hour in the presence of 10 ml of 2 N hydrochloric acid. The mixture was cooled to ambient temperature and poured into 300 ml of ice-cooled water. Extraction was carried out with ethyl acetate and the organic phase was washed with salt water, dried, and the solvent was evaporated off. The residue was chromatographed on silica (ethyl acetate—cyclohexane (1—1)) and the fractions were collected with a Rf=0.14. After crystallization from methylene chloride and cyclohexane, 4.37 g of the expected product melting at 130° C. were obtained

| Analysis; C₁₅H₁₄F₃N₃O₂S; molecular weight = 357.36 | | | | | |
|---|---|---|---|---|---|
| | C % | H % | F % | N % | S % |
| Calculated | 50.42 | 3.95 | 15.95 | 11.76 | 8.97 |
| Found | 50.3 | 3.9 | 15.9 | 11.6 | 8.9 |

| IR Spectrum (CHCl₃); | |
|---|---|
| OH | 3626 cm$^{-1}$ |
| C≡N | 2236 cm$^{-1}$ |
| C=O | 1763 cm$^{-1}$ |
| Aromatics | 1615-1578-1504 cm$^{-1}$ |

EXAMPLE 72

4-(4,4-dimethyl-3-(2-hydroxyethyl)-5-imino-2-thioxo 1-imidazolidinyl) 2-(trifluoromethyl)-5-³H-benzonitrile a) Preparation of the tritiated benzonitrile 15 mg of 2-trifluoromethyl 4-amino 5-bromo benzonitrile were mixed with 200 μl of ethyl acetate in the presence of 6.5 μl of triethylamine and 2 mg of palladium on activated charcoal and then tritium (1.42 bar) was introduced. After filtering, rinsing with ethyl acetate and evaporating to dryness at ambient temperature, approximately 66.6 G.Bq (1.8 Ci) of product were obtained.

b) Preparation of the tritiated isothiocyanate

150 μl of a 10% solution of thiophosgene in chloroform were added to the above product, in 150 μl of water and the mixture was stirred for 45 minutes at ambient temperature. Dilution was carried out with 0.5 ml of water and 1 ml of chloroform, followed by extraction with chloroform. The solvent was evaporated off under reduced pressure and the residue was taken up in toluene to obtain 50.7 G.Bq (1.37 Ci) of the expected product which was kept at −80° C.

c) Preparation of the tritiated imine

Having eliminated the toluene from the above mixture under reduced pressure, 130 μl of tetrahydrofuran with 1% triethylamine were added and 13 μl of 2-[(2-hydroxyethyl)-amino] 2-methylpropane-nitrile (Example 22)—were added. Then, another 130 μl of tetrahydrofuran with 1% triethylamine were added and the mixture was stirred for 30 minutes at ambient temperature and the solvents were eliminated under reduced pressure.

Preparation of the 2-trifluoromethyl 4-amino 5-bromo benzonitrile used in Example 72.

A solution of 2-trifluoromethyl 4-amino benzonitrile (prepared according to EP 0002892) (5 moles) in 25 ml of methanol was cooled to 0° C. and bomine was added (5.2 moles). The mixture was allowed to return to ambient temperature, stirred for 3 hours, alkalinized with triethylamine and then an aqueous solution of sodium thiosulfate was added. The solvents were eliminated and extraction was carried out with chloroform. The organic phase was washed with water, dried, and the solvent was evaporated to obtain the product which was used as is for the following stage.

| IR Spectrum (CHCl₃); | |
|---|---|
| NH₂ | 3612-3408 cm$^{-1}$ |
| C≡N | 2230 cm$^{-1}$ |
| Aromatics | 1621-1556-1506 cm$^{-1}$ |

EXAMPLE 73

4-(4,4-dimethyl-3-(2-hydroxyethyl)-5-oxo-2-thioxo 1-imidazolidinyl)-2-(trifluoromethyl) 5-³H-benzonitrile The product of Example 72 in 180 μl of water was heated to 100° C. and 60 μl of 2 N hydrochloric acid was added. The mixture was stirred for 5 minutes at reflux and then approximately 600 mg of ice were added. Extraction is carried out with ethyl acetate and the extracts were washed with salt water and dried to obtain 34.7 G.Bq (937 mCi) of product. After chromatography on silica (eluant: cyclohexane—ethyl acetate (60-40)), 19 G.Bq (513 mCi) of the expected product were obtained.

EXAMPLE 74

4-(4,4-dimethyl-3-hydroxypropyl)-5-imino-2-thioxo-1-imidazolidinyl) 2-(trifluoromethyl)-benzonitrile Using the procedure of Example 22—2 g of the isothio-cyanate of Example 70 (a) and 1.2 g of the appropriate aminonitrile were reacted to obtain 1.70 g of the expected product with a Rf=0.25 (methylene chloride—acetone (65-35)).

| IR Spectrum (CHCl₃); | |
|---|---|
| OH | 3630 cm⁻¹ |
| =NH | 3314-1676 cm⁻¹ |
| C≡N | 2235 cm⁻¹ |

EXAMPLE 75

4-(4,4-dimethyl-3-(3-hydroxypropyl)-5-oxo-2-thioxo-1-imidazolidinyl) 2-(trifluoromethyl) benzonitrile Using the procedure of Example 71, 240 mg of the product of Example 74 were reacted to obtain 226 mg of the expected product melting at 149°-150° C. with a Rf=0.32 (eluant; methylene chloride—acetone (75-25)).

| IR Spectrum (CHCl₃); | |
|---|---|
| OH | 3626 cm⁻¹ |
| C=O | 1763 cm⁻¹ |
| C≡N | 2236 cm⁻¹ |
| Aromatics | 1615-1580-1504-1483 cm⁻¹ |

EXAMPLE 76

4-(4,4-dimethyl 3-(4-hydroxybutyl)-5-imino 2-thioxo 1-imidazolidinyl) 2-(trifluoromethyl) benzonitrile Using the procedure of Example 22,—2 g of isothiocyanate and 1.38 g of the appropriate aminoitrile were reacted to obtain 2.08 g of the expected product with a Rf=0.25 (methylene chloride—acetone (65-35)).

| IR Spectrum (CHCl₃); | |
|---|---|
| OH | 3630 cm⁻¹ |
| =NH | 3314-1675 cm⁻¹ |
| C≡N | 2235 cm⁻¹ |
| Aromatics | 1614-1577-1504 cm⁻¹ |

EXAMPLE 77

4-(4,4-dimethyl 3-(4-hydroxybutyl)-5-oxo 2-thioxo-1-imidazolidinyl) 2-(trifluoromethyl) benzonitile Using the procedure of Example 71, 300 mg of the product of Example 76 were reacted to obtain 236 mg of the expected product melting at 78°-79° C. with a Rf=0.31 (eluant: methylene chloride—acetone (75-25)).

| IR Spectrum (CHCl₃); | |
|---|---|
| OH | 3624 cm⁻¹ |
| C=O | 1762 cm⁻¹ |
| C≡N | 2237 cm⁻¹ |
| Aromatics | 1615-1580-1504 cm⁻¹ |

| UV Spectrum (EtOH) | |
|---|---|
| Max. 232 nm | ε = 19500 |
| Max. 254 nm | ε = 24000 |
| Infl. 266 nm | |

EXAMPLE 78

4-(4,4-dimethyl 3-(2-methoxyethyl) 5-imino 2-thioxo 1-imidazolidinyl) 2-(trifluoromethyl) benzonitrile Using the procedure of Example 22,—2.5 g of isothiocyanate and 1.56 g of the appropriate aminoitrile were reacted to obtain 2.36 g of the expected product with a Rf=0.23 (methylene chloride—acetone (92.5-7.5)).

| IR Spectrum (CHCl₃); | |
|---|---|
| =NH | 3314 cm⁻¹ |
| C≡N | 2236 cm⁻¹ |
| Aromatics | 1614-1578-1504 cm⁻¹ |
| C=N | 1675 cm⁻¹ |

EXAMPLE 79

4-(4,4-dimethyl 3-(2-methoxyethyl) 5-oxo 2-thioxo 1-imidazolidinyl) 2-(trifluoromethyl) benzonitrile Using the procedure of Example 71, the product of Example 78 was reacted to obtain the expected product melting at 98°-99° C. with a Rf=0.32 (eluant: methylene chloride—acetone (99-1))

| IR Spectrum (CHCl₃); | |
|---|---|
| C=O | 1757 cm⁻¹ |
| C≡N | 2236 cm⁻¹ |
| Aromatics | 1615-1580-1504 cm⁻¹ |

| UV Spectrum (EtOH) | |
|---|---|
| Max. 232 nm | ε = 18200 |
| Max. 254 nm | ε = 22400 |
| Infl. 265 nm | |

EXAMPLE 80

4-(4,4-dimethyl 3-(1-methylethyl) 5-imino 2-thioxo 1-imidazolidinyl) 2-(trifluoromethyl) benzonitrile Using the procedure of Example 22,—2.5 g of the isothiocyanate and 1.32 g of the appropriate aminonitrile were reacted to obtain 880 mg of the expected product with a Rf=0.20 (eluant: methylene chloride—acetone (96-4)).

| IR Spectrum (CHCl$_3$); | |
|---|---|
| =NH | 3310-1675 cm$^{-1}$ |
| C≡N | 2236 cm$^{-1}$ |
| Aromatics | 1614-1580-1504 cm$^{-1}$ |

EXAMPLE 81

4-(4,4-dimethyl 3-(1-methylethyl) 5-oxo 2-thioxo 1-imidazolidinyl) 2-(trifluoromethyl) benzonitrile Using the procedure of Example 71, 880 mg of the product of Example 80 and 35 ml of 6 N hydrochloric acid were reacted to obtain after extraction with chloroform, 744 mg of the expected product melting at 203°-204° C. with a Rf=0.45 (eluant: cyclohexane—ethyl acetate (1—1)).

| IR Spectrum (CHCl$_3$); | |
|---|---|
| OH | 3626 cm$^{-1}$ |
| C=O | 1753 cm$^{-1}$ |
| C≡N | 2232 cm$^{-1}$ |
| Aromatics | 1615-1580-1504 cm$^{-1}$ |

| UV Spectrum (EtOH) | |
|---|---|
| Max. 232 nm | $\epsilon$ = 18900 |
| Max. 235 nm | $\epsilon$ = 22500 |
| Infl. 273 nm | |

EXAMPLE 82

3-(3,4-dichlorophenyl 5,5-dimethyl 1-(3-hydroxypropyl) 4-imino 2-imidazolidine thione Using the procedure of Example 51,—2.4 g of 3,4-dichlorophenyl isocyanate and 1.6 g of the appropriate aminonitrile were reacted to obtain, after chromatography on silica (eluant: methylene chloride—acetone (6-4)), 2.16 g of expected product with a Rf=0.25

| IR Spectrum (CHCl$_3$); | |
|---|---|
| OH | 3630 cm$^{-1}$ + associated |
| C=NH | 3294-1676 cm$^{-1}$ (F) |
| Aromatics | 1595-1569-1482 cm$^{-1}$ |

EXAMPLE 83

3-(3,4-dichlorophenyl 5,5-dimethyl 1-(3-hydroxypropyl) 2-thioxo 4-imidazolidinone Using the procedure of Example 52,—0.88 g of the product of Example 82 and 35 ml of 6 N hydrochloric acid were reacted to obtain, after extraction with chloroform, 0.79 g of the expected product melting at 202°-203° C.

| IR Spectrum (CHCl$_3$); | |
|---|---|
| C=O | 1753 cm$^{-1}$ |
| C≡N | 2232 cm$^{-1}$ |
| Aromatics | 1615-1580-1504 cm$^{-1}$ |

| UV Spectrum (EtOH) | |
|---|---|
| Max. 232 nm | $\epsilon$ = 18900 |
| Max. 235 nm | $\epsilon$ = 22500 |
| Infl. 273 nm | |

EXAMPLE 84

4-(4,4-dimethyl 3-(4-hydroxybutyl) 5-imino 2-thioxo 1-imidazolidinyl) 2-(trifluoromethyl) (5-$^3$H) benzonitrile a) 4-amino 2-(trifluoromethyl) (5-$^3$H) benzonitrile The following were cooled to $-180°$ C. and mixed under an inert atmosphere: 16 mg of 2-trifluoromethyl 4-amino 5-bromo benzonitrile, 2 mg of palladium on activated charcoal, 200 $\mu$l of ethyl acetate and 6.5 $\mu$l of triethylamine. Then the mixture was left under a tritium atmosphere and taken to 20° C. and the pressure was then 1.68 bar. The mixture was stirred until absorption was complete (p=0.42 bar), followed by cooling to $-180°$ C. The excess tritium was recovered, taken to 20° C. and then filtered. The filtrate was rinsed with ethyl acetate and concentrated at 40° C. under reduced pressure to obtain 68 G.Bq of the expected product.

b) 4-thioisocyanate 2-(trifluoromethyl) (5-$^3$H) benzonitrile

The following were mixed under an argon atmosphere: 34 G.Bq of the above tritiated amino derivate, 150 $\mu$l of demineralized water and 150 $\mu$l of 10% thiophosgene solution in chloroform. The mixture was stirred at 20° C. for 45 minutes, decanted and reextraction was carried out with chloroform. The extracts were dried over magnesium sulfate, filtered and concentrated under reduced pressure. The thioisocyanate obtained was used as is for the following stage.

c) 4-(4,4-dimethyl 3-(4-hydroxybutyl) 5-imino 2-thioxo 1-imidazolidinyl) 2-(trifluoromethyl) (5-$^3$H) benzonitrile The following were mixed under an argon atmosphere with the thioisocyanate of stage b): 350 $\mu$l of tetrahydrofuran with 1% triethylamine and 20 $\mu$l of propanonitrile prepared as indicated below. The mixture was stirred for 2 hours at 20° C., followed by concentration at 20° C. under reduced pressure. The imine was used as is for the following stage. Preparation of the 2-(4-hydroxybutylamino) 2-methylpropano-nitrile used in stage c)

550 $\mu$l of acetone cyanhydrin and 500 $\mu$l of 4-amino 1-butanol were mixed together and the mixture was stirred for 16 hours at 20° C. to obtain the desired product which was used as is for the following stage.

EXAMPLE 85

4-(4,4-dimethyl 3-(4-hydroxybutyl) 5-oxo 2-thioxo 1-imidazolidinyl) 2-(trifluoromethyl) (5-$^3$H) benzonitrile 200 μl of 2 N hydrochloric acid were added to the imine of Example 84 and the mixture was refluxed for 5 minutes, then returned to 20° C. and diluted with 1 ml of water. Extaction was carried out with ethyl acetate and the extracts were washed with water and concentrated under reduced pressure. The crude product was purified by chromatography on silica (eluant: cyclohexane—ethyl acetate (6-4)) to obtain 2.8 G.Bq of the expected product.

EXAMPLE 86

4-(4,4-dimethyl 3-(4-hydroxybutyl) 5-imino 2-thioxo 1-imidazolidinyl) 2-(trifluoromethyl) benzo ($^{14}$C) nitrile a) 4-amino 2-(trifluoromethyl) benzo ($^{14}$C) nitrile 377 mg of cuprous cyanide $^{14}$C (9 G.Bq) and 1.0732 g of 4-bromo 3-(trifluoromethyl) benzenamine were mixed together under a nitrogen atmosphere in 8 ml of dimethylformamide and the mixture was refluxed for 4 hours, then cooled to 0° C. and diluted with 20 ml of acetone. The insoluble part was filtered off and the filtrate was concentrated at 70° C. under reduced pressure. The residue was taken up in methylene chloride, filtered and the filtrate was concentrated under reduced pressure. The benzonitrile ($^{14}$C) was purified by chromatography on silica (eluant: methylene chloride—cyclohexane (70-30)) to obtain 0.558 g (6.62 G.Bq) of the expected product.

b) 4-thioisocyanate 2-(trifluoromethyl) benzo ($^{14}$C) nitrile

The following were mixed under a nitrogen atmosphere: 189 mg of benzonitrile ($^{14}$C) of stage a), 2.7 ml of water and 85 μl of thiophosgene. The mixture was agitated vigorously stirred for 5 minutes, and after 30 μl of thiophosgene were added, stirring was continued for one hour at 20° C. Then extraction was carried out with chloroform and the extracts were washed with water, dried and concentrated under reduced pressure. The thioisocyanate obtained was used as is for the following stage.

c) 4-(4,4-dimethyl 3-(4-hydroxybutyl) 5-imino 2-thioxo 1-imidazolidinyl) 2-(trifluoromethyl) benzo ($^{14}$C) nitrile 2 ml of tetrahydrofuran, the propanonitrile prepared below in solution in 1.5 ml of methylene chloride and 150 μl of triethylamine were added under a nitrogen atmosphere to the thioisocyanate of stage b). The mixture was heated for 30 minutes under reflux and concentrated under reduced pressure to obtain the imine which was used as is for the following stage.

Preparation of the 2-(4-hydroxybutylamino) 2-methylpropano-nitrile of stage c 220 μl of acetone cyanohydrin and 200 μl of 4-amino 1-butanol were mixed together with stirring for 16 hours at 20° C. and then was diluted with 2 ml of methylene chloride, dried, filtered and the filtrate was concentrated under reduced pressure to obtain the propanonitrile which was used as is for the following stage.

EXAMPLE 87

4-(4,4-dimethyl 3-(4-hydroxybutyl) 5-oxo 2-thioxo 1-imidazolidinyl) 2-(trifluoromethyl) benzo ($^{14}$C) nitrile 6 ml of methanol and 1.6 ml of 2 N hydrochloric acid were added to the imine of Example 86 and the mixture was refluxed for 45 minutes, cooled to 20° C. and diluted with 10 ml of water. Extraction was carried out with methylene chloride and the extracts were washed with water and concentrated under reduced pressure. The crude product was purified by chromatography on silica (eluant: ether—acetonitrile—cyclohexane (50-15-35)) to obtain 328 mg of the expected product.

EXAMPLE 88

4-(4,4-dimethyl 3-(4-hydroxybutyl) 5-imino 2-oxo 1-imidazolidinyl) 2-(trifluoromethyl) (5-$^3$H) benzonitrile a) 4-amino 2-(trifluoromethyl) (5-$^3$H) benzonitrile Using the procedure of stage a) of Example 84, 16 mg of 4-amino 5-bromo 2-trifluoromethyl benzonitrile, 2 mg of palladium on activated charcoal, 200 μl of ethyl acetate and 6.5 μl of triethylamine were reacted to obtain 68 G.Bq of the expected product.

b) 4-isocyanate 2-(trifluoromethyl) (5-$^3$H) benzonitrile

34 G.Bq of tritiated amino derivate of step a) and 100 μl of 20% phosgene in toluene were mixed together under an argon atmosphere and the mixture was taken to 80° C. for one hour. A further 100 μl of phosgene were added and the mixture heated for one hour at 80° C. This operation was repeated one more time, then concentration was carried out at 20° C. under reduced pressure to obtain the isocyanate which was used as is for the following stage.

c) 4-(4,4-dimethyl 3-(4-hydroxybutyl) 5-imino 2-oxo 1-imidazolidinyl) 2-(trifluoromethyl) (5-$^3$H) benzonitrile The following were added under an argon atmosphere to the isocyanate of stage b): 200 μl of methylene chloride, 50 μl of the propanonitrile chloromethylene solution prepared as below and 20 μl of triethylamine and the mixture was stirred for 30 minutes. A further 50 μl of the propanonitrile solution were added and stirring was continued for 30 minutes followed by concentration at 20° C. under reduced pressure. The imine was used as is for the following stage. Preparation of the 2-(4-hydroxybutylamino) 2-methyl propano-nitrile, of stage c)

220 μl of acetone cyanohydrin and 200 μl of 4-amino 1-butanol were mixed together and the mixture was stirred for 16 hours at 20° C., then diluted with 3 ml of methylene chloride and dried over magnesium sulfate. The decanted solution was used as is for the following stage.

EXAMPLE 89

4-(4,4-dimethyl2,5-dioxo 3-(4-hydroxybutyl) 1-imidazolidinyl) 2-(trifluoromethyl) (5-$^3$H) benzonitrile 200 μl of methanol and 50 μl of 2 N hydrochloric acid were added to the imine of Example 88 and the mixture was refluxed for 45 minutes, then returned to 20° C. and diluted with 1 ml of water. Extraction was carried out with methylene chloride and the extracts were washed with water and concentrated at 20° C. under reduced pressure. The crude product was purified by chromatography on silica (eluant: methylene chloride—ethyl acetate (7-3 then 5—5)) to obtain 16 G.Bq of the expected product.

EXAMPLE 90

4-(4,4-dimethyl 3-(4-hydroxybutyl) 5-imino 2-oxo 1-imidazolidinyl) 2-(trifluoromethyl) benzo ($^{14}$C) nitrile a) 4-amino 2-(trifluoromethyl) benzo ($^{14}$C) nitrile Using the procedure of Example 86, stage a), 377 mg of cuprous cyanide $^{14}$C, 1.0732 g of 4-bromo 3-trifluoromethyl benzenamine and 8 ml of dimethylformamide were reacted to obtain 0.558 g (6.62 G.Bq) of the expected product.

b) 4-isocyanato 2-(trifluoromethyl) benzo ($^{14}$C) nitrile 182.4 mg of benzonitrile ($^{14}$C) (0.97 mmole), 2 ml of dioxane and 1 ml of 20% phosgene in toluene were mixed together under a nitrogen atmosphere and the solution was heated at 60° C. for 22 hours, then concentrated at 60° C. under reduced pressure. The isocyanate was used as is for the following stage.

c) 4-(4,4-dimethyl 3-(4-hydroxybutyl) 5-imino 2-oxo 1-imidazolidinyl) 2-(trifluoromethyl) benzo ($^{14}$C) nitrile 1.5 ml of methylene chloride (on siliporite NK 30), the propanonitrile of Example 88 in solution in 1.5 ml of methylene chloride, and 150 μl of triethylamine were added under a nitrogen atmosphere to the isocyanate of stage b). The mixture was stirred for one hour at 20° C. and concentrated under reduced pressure. The imine was used as is for the following stage.

EXAMPLE 91

4-(4,4-dimethyl 2,5-dioxo 3-(4-hydroxybutyl) 1-imidazolidinyl) 2-(trifluoromethyl) benzo ($^{14}$C) nitrile 5 ml of methanol and 1.2 ml of 1 N hydrochloric acid were added to the imine of Example 90 and the mixture was refluxed for 40 minutes, then returned to 20° C. and diluted with 10 ml of water. Extraction was carried out with methylene chloride and the extracts were washed with water and concentrated under reduced pressure. The crude product was purified by chromatography on silica (eluant: ether—acetonitrile—cyclohexane (50-15-35)) to obtain 289 mg (1.26 G.Bq) of the expected product.

EXAMPLE 92

4-(2,5-dioxo 4,4-dimethyl 3-(4-triphenylmethoxy-butyl) 1-imidazolidinyl) 2-(trifluoromethyl) benzonitrile 370 mg of the product of Example 58, 307 mg of trityl chloride in the presence of 10 mg of 4-dimethylaminopyridine, 0.25 ml of triethylamine and 4 ml of dimethylformamide were stirred at ambient temperature for 16 hours. The mixture was heated to 40° C. for 4 hours, poured into water and extraction was carried out with ether. The extracts were washed with water and dried and the solvent was eliminated under reduced pressure. The residue was chromatographed on silica (eluant: cyclohexane—ethyl acetate 75-25) to obtain 467 mg of the expected product with a Rf=0.25.

| IR Spectrum (CHCl$_3$); | |
|---|---|
| C=O | 1778, 1725 cm$^{-1}$ (F) |
| C≡N | 2235 cm$^{-1}$ |
| Aromatics | 1615, 1597, 1505, 1490 cm$^{-1}$ |

EXAMPLE 93

4-(2,5-dioxo 4,4-dimethyl 3-(4-phenylmethoxy-butyl) 1-imidazolidinyl) 2-(trifluoromethyl) benzonitrile 48 mg of sodium hydride were added in several lots to 370 mg of the product of Example 58 in solution in 4 ml of dimethylformamide and the mixture was stirred for 30 minutes. Then, 0.12 ml of benzyl bromide and 40 mg of tetrabutylammonium iodide were added and after 90 minutes of reaction, the same amount of each reagent was added. The mixture was stirred for one hour and the reaction medium was poured into an ice-cooled aqueous solution of monopotassium phosphate. Extraction was carried out with ether and the extracts were washed with water and dried. The solvent was eliminated under reduced pressure and the residue was chromatographed on silica (eluant: methylene chloride—acetone 99-1) to obtain 140 mg of the expected product melting at 75°-76° C.

| IR Spectrum (CHCl$_3$); | |
|---|---|
| C=O | 1779, 1725 cm$^{-1}$ |
| C≡N | 2235 cm$^{-1}$ |
| Aromatics | 1615, 1580, 1505, 1497 cm$^{-1}$ |

EXAMPLE 94

4-[4,4-dimethyl 2,5-dioxo 3-(4-methoxybutyl) 1-imidazolidinyl] 2-(trifluoromethyl)-benzonitrile 50 mg of sodium hydride were added in several lots to 370 mg of the product of Example 58 in solution in 3 ml of dimethylformamide and the mixture was stirred for 20 minutes. 0.06 ml of methyl iodide were added and the mixture was stirred for one hour. A further 50 mg of sodium hydride were added and then after 20 minutes, 0.06 ml of methyl iodide were added. The reaction medium was poured into water and extracted with ether. The extracts were washed with water, dried and the solvent was evaporated. The residue was chromatographed on silica (eluant: methylene chloride—acetone 98-2) to obtain 135 mg of the expected product melting at 80°-81° C.

| IR Spectrum (CHCl$_3$); | |
|---|---|
| C=O | 1779, 1725 cm$^{-1}$ (F) |
| C≡N | 2234 cm$^{-1}$ |
| Aromatics | 1616, 1576, 1505 cm$^{-1}$ |
| OCH$_3$ approx. | 2830 cm$^{-1}$ |

EXAMPLE 95

4-[3-(4-chlorobutyl) 4,4-dimethyl 2,5-dioxo 1-imidazolidinyl] 2-(trifluoromethyl) benzonitrile Using the procedure of Example 59, 600 mg of the product of Example 8—and 660 mg of 1-chloro 4-iodobutane in solution in 1 ml of dimethylformamide cooled down to +5° C. were reacted to obtain 604 mg of the expected product melting at 80°-81° C.

| IR Spectrum (CHCl₃); | |
|---|---|
| C=O | 1779, 1725 cm⁻¹ (F) |
| C≡N | 2238 cm⁻¹ |
| Aromatics | 1616, 1575, 1505 cm⁻¹ |

EXAMPLE 96

4-[3-[4-[(methylsulphoneyl) oxyl] butyl] 4,4-dimethyl 2,5-dioxo 1-imidazolidinyl] 2-(trifluoromethyl) benzonitrile 0.17 ml of methanesulfonyl chloride were added to 740 mg of the product of Example 58 in solution in 7.4 ml of pyridine and 24 mg of 4-dimethylamino-pyridine and the mixture was stirred for one hour. The mixture was poured into ice-cooled water and extraction was carried out with methylene chloride. The extracts were washed with water and the residual pyridine was eliminated by distillation. The residue was chromatographed on silica (eluant: methylene chloride—ethyl acetate 8-2) to obtain 771 mg of the expected product.

| IR Spectrum (CHCl₃); | |
|---|---|
| C=O | 1779, 1725 cm⁻¹ |
| C≡N | 2235 cm⁻¹ |
| Aromatics | 1615, 1575, 1505 cm⁻¹ |
| $\begin{array}{c} O \\ \parallel \\ -OS- \\ \parallel \\ O \end{array}$ | 1361, 1175 cm⁻¹ |

| UV Spectrum (EtOH) | | |
|---|---|---|
| max. | 261 nm | ε = 14900 |
| infl. | 279–297 nm | |

EXAMPLE 97

4-(3-acetyl 4,4-dimethyl 2,5-dioxo 1-imidazo-lidinyl) 2-(trifluoromethyl) benzonitrile Using the procedure of Example 59, 420 mg of the product of Example 8—and two lots of 0.1 ml of acetyl chloride were reacted to obtain after chromatography on silica (eluant: methylene chloride—ethyl acetate 98-2), 334 mg of the expected product melting at 129°–130° C.

| IR Spectrum (CHCl₃); | |
|---|---|
| C=O | 1800, 1740, 1717 cm⁻¹ |
| C≡N | 2240 cm⁻¹ |
| Aromatics | 1616, 1505 cm⁻¹ |

| UV Spectrum (EtOH) | | |
|---|---|---|
| max | 250 nm | ε = 12000 |
| infl. | 274–284 nm | |

EXAMPLE 98

4-(3-benzoyl 4,4-dimethyl 2,5-dioxo 1-imidazolidinyl) 2-(trifluoromethyl) benzonitrile Using the procedure of Example 59, 300 mg of the product of Example 8—and two lots of 0.12 ml of benzoyl chloride in solution in 0.5 ml of dimethylformamide were reacted to obtain after chromatography on silica (eluant: cyclohexane—ethyl acetate 8-2), 285 mg of the expected product melting at 179°–180° C.

| IR Spectrum (CHCl₃); | |
|---|---|
| C=O | 1800, 1780, 1746, 1699 cm⁻¹ |
| C≡N | 2235 cm⁻¹ |
| Aromatics | 1617, 1600, 1580, 1504 cm⁻¹ |

| UV Spectrum (EtOH) | |
|---|---|
| max. 250 nm | ε = 28500 |
| infl. 275 nm | ε = 6500 |
| infl. 263 nm | ε = 3850 |

EXAMPLE 99

4-[3-[dimethyl (1,1-dimethylethyl) silyl] 4,4-dimethyl 2,5-dioxo 1-imidazolidinyl] 2-(trifluoromethyl) benzonitrle Using the procedure of Example 59, 450 mg of the product of Example 8—and 300 mg of dimethyl t-butyl-silyl chloride in 2 ml of dimethylformamide were reacted to obtain after chromatography on silica (eluant: methylene chloride—acetone 99-1), 527 mg of the expected product melting at 147°–148° C.

| IR Spectrum (CHCl₃); | |
|---|---|
| C≡N | 2236 cm⁻¹ |
| Aromatics | 1615, 1579, 1505 cm⁻¹ |

| UV Spectrum (EtOH) | |
|---|---|
| max. 258 nm | ε = 17000 |
| infl. 275–285 nm | |

In addition to the products described above, the following products are products which can be obtained within the scope of the present invention, namely the products of the formula:

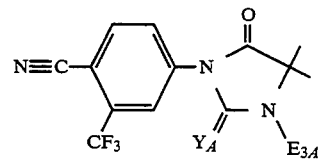

in which $Y_A$ is oxygen or sulfur and $R_{3A}$ has the following values:

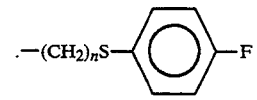

-continued

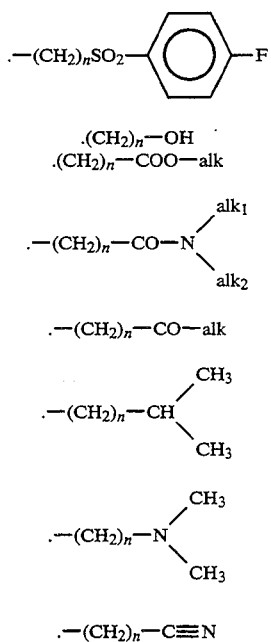

.—(CH$_2$)$_n$—OH
.(CH$_2$)$_n$—COO—alk

.—(CH$_2$)$_n$—CO—N⟨alk$_1$, alk$_2$

.—(CH$_2$)$_n$—CO—alk

.—(CH$_2$)$_n$—CH⟨CH$_3$, CH$_3$

.—(CH$_2$)$_n$—N⟨CH$_3$, CH$_3$

.—(CH$_2$)$_n$—C≡N alk, alk$_1$ and alk$_2$ are alkyl of 1 to 4 carbon atoms and n is an integer between 1 and 4.

EXAMPLE 100

Tablets were prepared with a composition of 100 mg of 4-(5-oxo-2-thioxo-3,4,4-trimethyl 1-imidazolinyl)-2-trifluoromethyl-benzonitrile and sufficient excipient of lactose, starch, talc and magnesium stearate for a final tablet weight of 300 mg.

PHARMACOLOGICAL DATA

Study of the affinity of the products of the invention for the androgenic receptor.

1) Androgenic receptor

Male rats of the Sprague Dawley EOPS strain weighing 180 to 200 g, castrated 24 hours previously, were killed and the prostrate was removed, weighed and homogenized at 0° C. with a potter glass in a buffered solution (Tris 10 mM, saccharose 0.25 M, PMSF (phenyl methane sulfonyl fluoride) 0.1 mM, sodium molybdate 20 mM, HCl pH 7.4 into which was added extemporaneously 2 M of DTT (DL dithiothreitol) at a rate of 1 g of tissue per 8 ml of buffer solution. The homogenate was then ultracentrifuged at 0° C. for 45 minutes at 105,000 g and the aliquots of supernatant (=cytosol) were incubated for 30 minutes and 24 hours with a concentration (T) of tritiated testosterone and in the presence of increasing concentrations (0 to 2500.10$^{-9}$M) of cold testosterone or the test products. The concentration of bound tritiated Testostrone (B) was then measured for each incubate by adsorption method of carbon-dextran. The relative affinity of bonding (RBA) was calculated.

The following two curves were graphed: the percentage of the bound tritiated hormone B/T as a logarithm function of the concentration of the cold hormone and B/T as a logarithm function of the concentration of the tested cold product. The line of the equation $$I_{50} = \frac{(B/T\max + B/T\min)}{2}$$

was determined. B/T max=% of the bound tritiated hormone for an incubation of this tritiated hormone at the concentration (T). B/T min=% of the bound tritiated hormone for an incubation of this tritiated hormone at the concentration (T) in the presence of a large excess of cold hormone (2,500×10$^{-9}$M).

The intersections of the straight line I$_{50}$ and the curves permit an evaluation of the concentrations of the cold reference hormones (CH) and the cold test product (CX) which inhibit by 50% the bonding of the tritiated hormone on the receptor. The RBA 9of the test product was determined by the equation

RBA=(CH)/(CX)

and the following results expressed in ARL were obtained with testosterone=100.

|  | Incubation 30 minutes | Incubation 24 hours |
|---|---|---|
| Product Example 1 | 27.5 | 3 |
| Product Example 2 | 22 | 6 |
| Product Example 4 | 21 | 5 |
| Product Example 11 | 28 | 8 |
| Product Example 12 | 128 | 92 |
| Product Example 13 | 31 | 39 |
| Product Example 14 | 27 | 7 |
| Product Example 15 | 69 | 24 |

2) Study of the affinity of the products of the invention for the androgen receptor.

Male rats of the Sprague Dawley EOPS strain weighing 180 to 200 g, castrated 24 hours previously, were killed and the prostate was removed, weighed and homogenized at 0° C. with a potter glass in a buffered solution (Tris 10 mM, saccharose 0.25 M, PMSF (phenyl methane sulfonyl fluoride) 0.1 mM, sodium molybdate 20 mM, HCl pH 7.4 into which was added extemporaneously 2 mM of DTT (DL dithiothreitol) at a rate of 1 g of tissue per 8 ml of buffer solution. The homogenate was then ultracentrifuged at 0° C. for 30 minutes at 209,000 g and the aliquots of supernatant (=cytosol) were incubated for 30 minutes and 24 hours with a concentration (T) of tritiated testosterone and in the presence of increasing concentrations (0 to 2500.10$^{-9}$M) of cold testosterone or the test products. The concentration of bound tritiated Testostrone (B) was then measured for each incubate by adsorption method of carbon-dextran. The relative affinity of bonding (RBA) was calculated.

The following two curves were graphed: the percentage of the bound tritiated hormone B/T as a logarithm function of the concentration of the cold hormone and B/T as a logarithm function of the concentration of the tested cold product. The line of the equation $$I_{50} = \frac{(B/T\max + B/T\min)}{2}$$

was determined. B/T max=% of the bound tritiated hormone for an incubation of this tritiated hormone at the concentration (T). B/T min=% of the bound triti-ated hormone for an incubation of this tritiated hormone at the concentration (T) in the presence of a large excess of cold hormone ($2,500 \times 10^{-9}$ M).

The intersections of the straight line $I_{50}$ and the curves permit an evaluation of the concentrations of the cold reference hormones (CH) and the cold test product (CX) which inhibit by 50% the bonding of the tritiated hormone on the receptor. The RBA of the test product was determined by the equation $$RBA = 100(CH)/(CX)$$

and the following results expressed in RBA were obtained with testosterone=100.

|  | Incubation 24 hours |
|---|---|
| Example 59 | 31 |
| Example 71 | 163 |
| Example 77 | 300 |
| Example 79 | 81 |
| Example 81 | 28 |

3) Determination of the androgen or anti-androgen activity by the dosage of ornithine carboxylase.

Six week old male Swiss mice castrated 24 hours receive oral does of the test products as a 0.5% suspension in methyl cellulose simultaneously with a sub-cutaneous injection of 3 mg/kg of testosterone propionate in solution in sesame oil containing 5% of benzyl alcohol to determine the anti-androgen activity. Active agonists were determined in the absence of testosterone propionate. The test compounds as well as testosterone were administered in a volume of 10 ml/kg. 16 hours after the treatments, the animals were killed, the kidneys were removed and then homogenized at 0° C. with a teflon-glass grinding apparatus in 10 volumes of buffer Tris-HCl 50 mM at a pH 7.4 containing 250 mM of pyridoxal phosphate, 0.1 mM EDTA and 5 mM of dithiothreitol. The homogenate was centrifuged at 105,000 g for 45 minutes.

At 37° C., renal ornithine decarboxylase transforms an isotropic mixture of cold ornithine and tritiated ornithine in cold putrescine and tritiated putrescine. The putrescine was then collected on selective ion-exchange papers. After drying, excess non-transformed cold and tritiated ornithine were eliminated by washing 3 times with 0.1 M ammonium hydroxide. The papers were dried and the radioactivity was determined after addition of an Aqualite sample. The results expressed in fmoles ($10^{-15}$ M) of tritiated putrescine formed per hour mg of protein are reported in the following Table

| PRODUCT OF EXAMPLE | ANTAGONISM IN MG/KG | PERCENT |
|---|---|---|
| 11 | 3 | 83 |
| 12 | 0.1 | 12 |
|  | 0.3 | 36 |
|  | 1 | 68 |
|  | 3 | 94 |
|  | 10 | 99 |
| 12 | (Agonism) 10 | 0 |
| 14 | Antagonism 3 | 87 |
| 15 | 0.3 | 4 |
|  | 1 | 82 |

4) Determination of the androgen or anti-androgen activity by the dosage of ornithine carboxylase.

Swiss six week old male mice castrated 24 hours received oral or percutaneous doses of the test products as a 0.5% suspension in methyl cellulose or in ethanol simultaneously with a sub-cutaneous injection of 3 mg/kg of testosterone propionate in solution in corn oil to determine the anti-androgen activity. Active agonists were determined in the absence of testosterone propionate. The test compounds as well as testosterone were administered in a volume of 10 ml/kg. 20 hours after the treatments, the animals were killed, the kidneys were removed and then homogenized at 0° C. with a teflon-glass grinding apparatus in 10 volumes of buffer Tris-HCl 50 mM at a pH 7.4 containing 250 mM of pyridoxal phosphate, 0.1 mM EDTA and 5 mM of dithiothreitol. The homogenate was centrifuged at 209,000 g for 45 minutes.

Principle of dosage

At 37° C., renal ornithine decarboxylase transforms an isotopic mixture of cold ornithine and tritiated ornithine in cold putrescine and tritiated putrescine. The putrescine was then collected on selective ion-exchange papers. After drying, excess non-transformed cold and tritiated ornithine were eliminated by washing 3 times with 0.1 M ammonium hydroxide. The papers were dried and the radioactivity was determined after addition of an Aqualite sample. The results expressed in fmoles ($10^{-15}$ M) of tritiated putrescine formed per hour/mg of protein are reported in the following Table.

The same test were repeated with the following changes:

Test A: the products were administered percutaneously at 1.5 mg/kg at a volume of 10 µl.

Test B: the products were administered orally at 1 mg/kg.

Test C: the products are administered orally at 3 mg/kg. The results are in the following Table.

The results are expressed in % of inhibition of the ODL the samples receiving only the testosterone propionate:

| Products of example | ODL | | |
|---|---|---|---|
|  | Test A | Test B | Test C |
| 58 | 40 | 36 |  |
| 71 | 32 |  | 67 |
| 75 | 41 |  |  |
| 78 | 78 |  |  |
| 80 | 62 |  |  |
| 81 | 35 |  |  |
| 83 | 58 |  |  |

CONCLUSION

The tests show that the tested compounds of the invention possess a strong anti-androgen activity and do not have agonist activity.

Various modifications of the compounds and method of the invention may be made without departing from the spirit or scope thereof and it is to be understood that the invention is intended to be limited only as defined in the appended claims.

We claim:

1. A compound selected from the group consisting of a compound of the formula

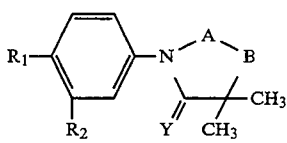 I wherein $R_1$ is selected from the group consisting of —CN, —NO$_2$ and halogen, $R_2$ is —CF$_3$ or halogen, —A–B is

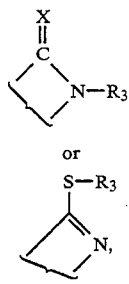

X is —O— or —S—, R$_3$ is selected from the group consisting of a) hydrogen, b) alkyl, alkenyl and alkynyl of up to 12 carbon atoms, c) phenyl and phenylalkyl unsubstituted or substituted with at least one member of the group consisting of —OH, halogen, —OCH$_3$, —CN and haloalkyl, d) acyl of an organic carboxylic acid of up to 7 carbon atoms, e) free or salified carboxy, carboxy esterified with alkyl and amidified carboxy, f) amino and mono and dialkylamino of 1 to 4 carbon atoms and g) —S—phenyl unsubstituted or substituted with at least one member of the group consisting of—CF$_3$ and alkyl, alkenyl, alkoxy, alkenyloxy, alkynyl and alkynyloxy of up to 12 carbon atoms with the sulfur unoxidized or oxidized to sulfone or sulfoxide, the alkyl, alkenyl and alkynyl being uninterrupted or interrupted with oxygen, sulfur or nitrogen and Y is —O—, —S— or —NH— with the provisos that when X is oxygen, R$_3$ is hydrogen and Y is —O— or —NH—, then R$_1$ is NO$_2$ or —CN and when X is sulfur and Y is —O— then at least one of the following conditions is satisfied, R$_1$ is —CN and R$_2$ is —CF$_3$ and their non-toxic, pharmaceutically acceptable acid addition salts.

2. A compound of claim 1 wherein Y is oxygen.

3. A compound of claim 1 wherein —A–B— is

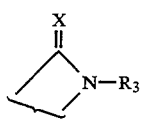

and X is sulfur.

4. A compound of claim 3 wherein R$_3$ is hydrogen or alkyl of 1 to 4 carbon atoms optionally substituted with a —OH or methoxy.

5. A compound of claim 1 wherein R$_1$ is —CN or halogen.

6. A compound of claim 1 wherein R$_1$ wherein R$_1$ is chlorine.

7. A compound of claim 1 wherein —A–B— is

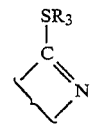

or

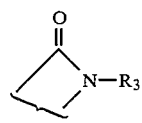

and R$_3$ is alkyl or alkenyl of up to 6 carbon atoms unsubstituted or substituted or uninterrupted or interrupted by oxygen or unoxidized or oxidized sulfur or unsubstituted or substituted aralkyl or acylor trialkylsilyl.

8. A compound of claim 7 wherein R$_3$ is alkyl of 1 to 6 carbon atoms unsubstituted or substituted by at least one member of the group consisting of halogen, —OH, —O acyl, carboxy, carboxy esterified with alkyl, a heterocycle, O-alkyl and unoxidized or oxidized S-aryl with the aryl unsubstituted or substituted with at least one member of the group consisting of halogen and alkoxy.

9. A compound of claim 8 wherein R$_3$ is alkyl of 2 to 4 carbon atoms substituted by a member selected from the group consisting of chlorine, ethoxycarbonyl, tertbitoxy carbonyl, cyclopentyloxycarbonyl, unoxidized or oxidized 4-fluorophenylthio, morpholino, phenylmethoxy, triphenylmethoxy and methylsulfonyloxy.

10. A compound of claim 7 wherein R$_3$ is acetyl or benzoyl or (1,1-dimethylethyl)dimethylsilyl.

11. A compound of claim 1 selected from the group consisting of 4-(5-oxo-2-thioxo-3,4,4-trimethyl-1-imidazolidinyl)-2-(trifluoromethyl) benzonitrile, 4-(4,4-dimethyl-5-oxo-2-thioxo 1-imidazolidinyl)-2-(trifluoromethyl)-benzonitrile, 4-4,4-dimethyl-3-(2-hydroxyethyl)-5-oxo-2-thioxo-1-imidazolidinyl 2-(trifluoromethyl)-benzonitrile, 3-(3,4-dichlorophenyl)-2-thioxo--1,5,5-trimethyl-4-imidazolidinone, 1-(4-nitro-3-(trifluoromethyl) phenyl-3,4,4-trimethyl-2,5-imidazolidinedione, 4-4,5-dihydro4,4-dimethyl-5-oxo-2-(phenylmethyl) thio-1H-imidazol-1-yl-2-(trifluoromethyl) benzonitrile, 4 4,4-dimethyl 3-(2-hydroxyethyl) 5-oxo 2-thioxo 1-imidazolidinyl 2-(trifluoromethyl) benzonitrile, 4-(4,4-dimethyl 3-(4-hydroxybutyl) 5-oxo 2-thioxo 1-imidazolidinyl) 2-(trifluoromethyl) benzonitrile, 3-(4-cyano 3-trifluoromethyl) phenyl) 5,5-dimethyl 2,4-dioxo 1-imidazolidinebutanoic acid and 4-(4,4-dimethyl 2,5-dioxo 3-(4-hydroxybutyl) 1-imidazolidinyl) 2-(trifluoromethyl benzonitrile.

12. A compound of claim 1 wherein Y is —O— except the compounds wherein the —A–B— group is

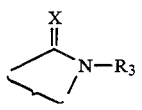

in which X is oxygen and R$_3$ is hydrogen, R$_2$ is halogen or trifluoromethyl and R$_1$ is nitro or halogen.

13. A compound of the formula

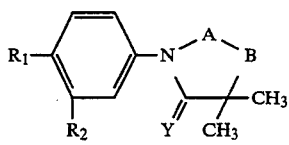

wherein $R_1$, $R_2$ and Y have the definitions of claim 1, —A—$_i$—B$_1$ is

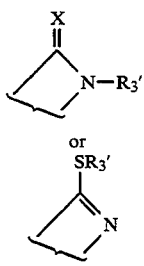

Y is oxygen or sulfur and $R'_3$ is $R_3$ with any reactive functions protected.

14. An anti-androgenic composition comprising an anti-androgenically effective amount of at least one compound of claim 1 and an inert pharmaceutical carrier.

15. A composition of claim 14 wherein the active compound is selected from the group consisting of 4-(5-oxo-2-thioxo-3,4,4-trimethyl-1-imidazolidinyl) 2-(trifluoromethyl)-benzonitrile, 4-(4,4-dimethyl-5-oxo-2-thioxo 1-imidazolidinyl) 2-(trifluoromethyl)-benzoitrile, 4-4,4-dimethyl-3-(2-hydroxyethyl)-5-oxo-2-thioxo 1-imidazolidinyl-2-(trifluoromethyl)-benzonitrile, 3-(3,4-dichlorophenyl) 2-thioxo- -1,5,5,-trimethyl-4-imidazolidinone, 1-(4-nitro-3-(trifluoromethyl)-phenyl-3,4,4-trimethyl-2.5-imidazolidinedione, 4-4,5-dihydro4,4-dimethyl-5-oxo-2-(phenylmethyl)thio-1H-imidazol 1-yl)2-(trifluoromethyl) benzonitrile-4,4,4-dimethyl 3-(2-hydroxyethyl) 5-oxo 2-thioxo 1-imidazolidinyl 2-(trifluoromethyl) benzonitrile, 4-(4,4-dimethyl 3-(4-hydroxybutyl) 5-oxo 2-thioxo 1-imidazolidinyl) 2-(trifluoromethyl) benzonitrile-3-(4-cyano 3-trifluoromethyl) phenyl) 5,5-dimethyl 2,4-dioxo 1-dioxo 3-(4-hydroxybutyl) 1- imidazolidinyl) 2-(trifluoromethyl) benzonitrile.

16. A method of inducing anti-androgenic activity in warm-blooded animals comprising administering to warm-blooded animals an anti-androgenically effective amount of at least one compound of claim 1.

17. A method of claim 16 wherein Y is oxygen.

18. A method of claim 16 wherein $R_1$ is —CN or halogen.

19. A method of claim 16 wherein $R_1$ is chlorine.

20. A method of claim 14 wherein the active compound is selected from the group consisting of 4-(5-oxo-2-thioxo-3,4,4-trimethyl-1-imidazolidinyl) 2-(trifluoromethyl)-benzonitrile, 4-(4,4-dimethyl-5-oxo-2-thioxo 1-imidazolidinyl)-2-(trifluoromethyl)-benzonitrile, 4-4,4-dimethyl-3-(2-hydroxyethyl) 5-oxo-2-thioxo-1-imidazolidinyl-2-(trifluoromethyl)-benzonitrile, 3-(3,4-dichlorophenyl)-2-thioxo- -1,5,5-trimethyl-4-imidazolidinone, 1-(4-nitro-3-(trifluoromethyl)-phenyl-3,4,4-trimethyl-2,5-imidazolidinedione, 4-4,5-dihydro4,4-dimethyl-5-oxo-2-(phenylmethyl)-thio-1H-imidazol-1-yl-2-(trifluoromethyl) benzonitrile-4,4,4-dimethyl 3-(2-hydroxyethyl) 5-oxo 2-thioxo 1-imidazolidinyl 2-(trifluoromethyl) benzonitrile, -4-(4,4-dimethyl 3-(4-hydroxybutyl) 5-oxo 2-thioxo 1-imidazolidinyl) 2-(trifluoromethyl) benzonitrile-3-(4-cyano 3-trifluoromethyl) phenyl) 5,5-dimethyl 2,4-dioxo 1-imidazolidinebutanoic and acid and 4-(4,4-dimethyl 2,5-dioxo 3-(4-hydroxybutyl) 1-imidazolidinyl) 2-(trifluoromethyl) benzonitrile.

* * * * *